United States Patent
Kondo et al.

[11] Patent Number: 6,082,176
[45] Date of Patent: Jul. 4, 2000

[54] NOX-CONCENTRATION DETECTING APPARATUS

[75] Inventors: Noriaki Kondo; Hiroshi Inagaki, both of Aichi, Japan

[73] Assignee: NGK Spark Plug Co., Ltd., Nagoya, Japan

[21] Appl. No.: 09/096,180

[22] Filed: Jun. 12, 1998

[30] Foreign Application Priority Data

Jun. 13, 1997 [JP] Japan .................................. 9-156875
Jun. 20, 1997 [JP] Japan .................................. 9-164477

[51] Int. Cl.$^7$ ............................ G01N 7/00; G01N 27/26; G01N 31/12
[52] U.S. Cl. ........................... 73/23.31; 422/94; 204/424; 73/31.05
[58] Field of Search ................................ 73/31.05, 31.06, 73/23.31, 23.2; 422/94, 90, 98, 83, 52, 95; 204/424, 425, 406

[56] References Cited

U.S. PATENT DOCUMENTS

| | | | |
|---|---|---|---|
| 3,970,430 | 7/1976 | Reader, Jr. et al. | 436/116 |
| 4,335,073 | 6/1982 | Sherwood et al. | 422/83 |
| 4,981,125 | 1/1991 | Kato et al. | |
| 5,034,112 | 7/1991 | Murase et al. | |
| 5,320,577 | 6/1994 | Tooru et al. | 454/75 |
| 5,389,340 | 2/1995 | Satake | 422/98 |
| 5,672,811 | 9/1997 | Kato et al. | 73/31.05 |
| 5,705,129 | 1/1998 | Takahashi et al. | 422/90 |
| 5,800,783 | 9/1998 | Nanaumi et al. | 422/94 |

FOREIGN PATENT DOCUMENTS

| | | | |
|---|---|---|---|
| 0 678 470 A1 | 10/1995 | European Pat. Off. | |
| 0678 740 A1 | 10/1995 | European Pat. Off. | G01N 27/407 |
| 0 769 693 A1 | 4/1997 | European Pat. Off. | |
| 0 810 430 A2 | 12/1997 | European Pat. Off. | |

OTHER PUBLICATIONS

*Patent Abstract of Japan*, vol. 017, No. 369 (P–1572), Jul. 12, 1993 & JP 05 060696 A (Shimadzu Corp.), Mar. 12, 1993.

*Primary Examiner*—Hezron Williams
*Attorney, Agent, or Firm*—Sughrue, Mion, Zinn, Macpeak & Seas, PLLC

[57] ABSTRACT

An NOx-concentration detecting apparatus is disclosed which enables a user to readily know a record of operating conditions of an NOx sensor. The apparatus includes an NOx sensor, pumping-current control means, constant-voltage application means, NOx-concentration detecting means, a heater and writing means for writing to a recorder variation of at least one parameter selected from a first pumping current value, a second pumping current value, the concentration of oxygen contained in the measurement gas and the concentration of NOx in the measurement gas. Also disclosed is an NOx-concentration detecting apparatus capable of determining the concentration of NOx at a high resolution even when different NOx sensors are used. The NOx-concentration detecting apparatus detects the first pumping current $I_{P1}$, and the second pumping current $I_{p2}$, corrects the detected values based on correction data stored on a floppy disk, and determines the concentration of NOx in the measurement gas using standard characteristics stored in ROM of the ECU, namely, characteristics representing correlations among the first pumping current $I_{P1}$, the second pumping current $I_{p2}$ and the concentration of NOx in the measurement gas. The correction data are used for making previously measured characteristics of the NOx sensor equal to the standard characteristics, which characteristics represent correlations among the first pumping current $I_{P1}$, the second pumping current $I_{p2}$ and the concentration of NOx in the measurement gas. Accordingly, when the concentration of NOx in the same measurement gas is measured using different NOx sensors, any of the NOx sensors can provide an accurate measurement.

29 Claims, 8 Drawing Sheets

NOX-CONCENTRATION DETECTING APPARATUS

BACKGROUND OF THE INVENTION

1. Field of the Invention

The present invention relates to an NOx-concentration detecting apparatus for detecting the concentration of nitrogen oxides, or harmful emissions, contained in exhaust gases from various combustion apparatus, including internal combustion engines.

2. Description of the Related Art

NOx-concentration detecting apparatus using an NOx sensor for detecting the concentration of nitrogen oxides (NOx) contained in exhaust gases from internal combustion engines and the like are disclosed, for example, in European Patent Application Laid-Open No. 0678740A1 and SAE Paper No. 960334, pp. 137–142, 1996. An NOx sensor used in such a conventional NOx-concentration detecting apparatus is composed of oxygen-ion conductive solid electrolyte layers that form a first measurement space and a second measurement space. The first measurement space communicates with the gas to be measured (hereinafter called "a measurement gas") via a first diffusion-controlling layer, and the second measurement space communicates with the first measurement space via a second diffusion-controlling layer. Furthermore, the solid electrolyte layer of the first measurement space is sandwiched between porous electrodes so as to form a first oxygen-pumping cell and an oxygen-concentration-measuring cell. Also, the solid electrolyte layer of the second measurement space is sandwiched between porous electrodes so as to form a second oxygen-pumping cell.

In the thus-configured NOx-concentration detecting apparatus, the first oxygen-pumping cell is energized so that an output voltage from the oxygen-concentration-measuring cell attains a predetermined value, thereby pumping out oxygen from the first measurement space and thus controlling the concentration of oxygen contained in the first measurement space at a constant level. At the same time, a constant voltage is applied to the second oxygen-pumping cell to thereby pump out oxygen from the second measurement space. As a result, the NOx concentration of a measurement gas can be obtained from current flowing through the second oxygen-pumping cell.

A measurement gas, e.g., exhaust from an internal combustion engine or the like, contains gas components other than NOx, such as oxygen, carbon monoxide and carbon dioxide. Thus, in the aforementioned NOx-concentration detecting apparatus, first, current is applied to the first oxygen-pumping cell to thereby pump out most of the oxygen from a measurement gas contained in the first measurement space. Then, in the second measurement space into which the oxygen-removed measurement gas flows, a constant voltage is applied to the second oxygen-pumping cell in a direction such that oxygen is pumped out from the second measurement space. As a result, NOx contained in the measurement gas is decomposed into nitrogen and oxygen by means of the catalyzing function of the porous electrodes of the second oxygen-pumping cell, and the thus-generated oxygen is then pumped out from the second measurement space. Thus, the NOx concentration of the measurement gas can be obtained from current flowing through the second oxygen-pumping cell without being influenced by other gas components contained in the measurement gas.

In such an NOx-concentration detecting apparatus, the concentration of nitrogen oxides is obtained based on current flowing through the second oxygen-pumping cell. The current flow is usually on the HA scale, and is considerably smaller than the current flowing through the first oxygen-pumping cell. When the current flowing through the second oxygen-pumping cell varies by 1 $\mu$A, the concentration of nitrogen oxides varies by 100 to 200 ppm. As a result, sensor operation is highly sensitive to operating conditions, so that the NOx sensor may become unusable under certain conditions. Also, when the concentration of NOx is measured at a high resolution of, for example, 1 ppm, the above microscopic variations in the concentration of nitrogen oxides present a significant measurement problem.

When the NOx sensor becomes unusable due to a failure or the like, knowledge of the operating conditions under which the NOx sensor had been used prior to that time is important in investigating the cause of the failure. If the cause can be identified, countermeasures can be taken so as to effectively improve the NOx sensor.

However, conventionally, when there was a need to know the operating conditions under which the failed NOx sensor was used, there was no choice but to inquire of an operator about his/her memory of the operating conditions. Thus, a problem with conventional NOx sensors is that it is difficult to make effective improvements.

Also, the concentration of NOx in the measurement gas is determined based on characteristics correlated to the current flowing through the first-oxygen pumping cell, the current flowing through the second oxygen-pumping cell, and the concentration of NOx in the measurement gas. However, these characteristics differ somewhat among NOx sensors. Accordingly, when the same correlations are used among a number of NOx sensors for measuring NOx concentration, a high degree of measurement accuracy may not be obtained.

SUMMARY OF THE INVENTION

The present invention has been accomplished in view of the above-mentioned problems of the prior art. Accordingly, a first object of the invention is to provide an NOx-concentration detecting apparatus capable of providing a record of its operating conditions. Yet another object of the present invention is to provide an NOx-concentration detecting apparatus capable of determining NOx concentration at high resolution even when different NOx sensors are used.

The above first object of the present invention has been achieved by providing an NOx-concentration detecting apparatus comprising an NOx sensor, pumping-current control means, constant-voltage application means, NOx-concentration detecting means and a heater.

The NOx sensor of the above first aspect of the invention comprises a first measurement space and a second measurement space. The first measurement space comprises a first oxygen-pumping cell and an oxygen-concentration-measuring cell and communicates with a measurement gas via a first diffusion-controlling layer. Each of the first oxygen-pumping cell and the oxygen-concentration-measuring cell is formed by an oxygen-ion conductive solid electrolyte layer and porous electrodes disposed on the opposite surfaces of the oxygen-ion conductive solid electrolyte layer. The second measurement space comprises a second oxygen-pumping cell and communicates with the first measurement space via a second diffusion-controlling layer. The second oxygen-pumping cell is formed by an oxygen-ion conductive solid electrolyte layer and porous electrodes disposed on opposite surfaces of the oxygen-ion conductive solid electrolyte layer.

The pumping-current control means controls the concentration of oxygen contained in the first measurement space at a constant level by pumping out oxygen from the first measurement space by means of the first oxygen-pumping cell such that an output voltage from the oxygen-concentration-measuring cell is maintained at a constant value.

The constant-voltage application means applies a constant voltage to the second oxygen-pumping cell in a direction (or polarity) such that oxygen is pumped out from the second measurement space.

The NOx-concentration detecting means determines the concentration of NOx in the measurement gas based on the value of current which flows through the second oxygen-pumping cell as a result of applying a constant voltage to the second oxygen-pumping cell.

The heater heats the NOx sensor to a temperature which enables detection of the concentration of NOx in the measurement gas.

The NOx-concentration detecting apparatus further comprises writing means for writing to recording means variation of at least one parameter selected from the group consisting of the value of current flowing through the first oxygen-pumping cell when controlled by the pumping-current control means (hereinafter referred to as a first pumping current value), the value of current flowing through the second oxygen-pumping cell when applying voltage to the second oxygen-pumping cell by the constant-voltage application means (hereinafter referred to as a second pumping current value), the concentration of oxygen contained in the measurement gas which is determined based on the first pumping current value, and the concentration of NOx in the measurement gas which is determined based on the second pumping current value.

As in the case of the aforementioned conventional NOx-concentration detecting apparatus, the NOx-concentration detecting apparatus of the first aspect of the present invention can determine the concentration of NOx in the measurement gas using the NOx sensor. Specifically, the heater heats the NOx sensor to a temperature which enables detection of the concentration of NOx in the measurement gas. The pumping-current control means controls the concentration of oxygen contained in the first measurement space to a constant level. The constant-voltage application means applies a constant voltage to the second oxygen-pumping cell in a direction (polarity) such that oxygen is pumped out from the second measurement space. The NOx-concentration detecting means determines the concentration of NOx in the measurement gas based on the value of current which flows through the second oxygen-pumping cell as a result of applying a constant voltage to the second oxygen-pumping cell.

In the first aspect of the present invention, the writing means writes to the recording means variation of at least one parameter selected from the group consisting of the first pumping current value, the second pumping current value, the concentration of oxygen contained in the measurement gas and the concentration of NOx in the measurement gas.

Therefore, according to the NOx-concentration detecting apparatus of the first aspect of the present invention, when the NOx sensor becomes unusable due to a failure or the like, a record of operating conditions of the sensor is available from the recording means. This feature facilitates investigation of the cause of a failure, so that a user can take appropriate measures and effectively improve the sensor. Also, sensor performance (e.g., durability and heat resistance) can be accurately evaluated.

In addition to the above-mentioned four parameters, other parameters related to detection of the concentration of NOx in the measurement gas may be recorded using the recording means.

Preferably, the writing means writes to the recording means, at predetermined intervals, variation of at least one parameter selected from the above parameter group. In this case, because variation of a parameter is recorded at predetermined intervals, when the NOx sensor becomes unusable, a user can readily identify when the sensor became unusable or when the sensor showed signs of becoming unusable.

Preferably, the writing means writes to the recording means variation of at least one parameter selected from the above parameter group, in the form of a maximum value and a minimum value in each period. In this case, the capacity of the recording means can be reduced as compared to the case of continuously recording changes in a parameter.

Preferably, the NOx sensor is removably connected to the NOx-concentration detecting means via a connector. In this case, for example, when the NOx sensor becomes unusable, the sensor may be replaced with a new one to thereby continue detection of NOx concentration and record the operating conditions of the sensor.

Preferably, the recording means comprises a removable recording medium. A removable recording medium can accompany the NOx sensor. Because a recording medium is used to record data concerning a specific NOx sensor, the recording medium preferably accompanies the sensor. Examples of such a recording medium include flexible disks (floppy disks and the like), optical disks and magneto-optical disks. Personal computers of popular use and like computers can read data from these recording media, and these recording media can be readily handled or carried. Also, preferably, the recording means is a button-like recording medium that can be removably mounted via a mount. Examples of such a recording medium include TOUCH MEMORY BUTTON, DS1995, (trade name, product of Dallas Semiconductor Corporation). Examples of the mount include TOUCH MEMORY MOUNT PRODUCT, DS9093x, (trade name, product of Dallas Semiconductor Corporation). In this case, the recording medium is smaller, and thus can be more readily handled or carried.

Preferably, the NOx sensor is removably connected to the NOx-concentration detecting means via a connector, and the recording means is built into the connector. Examples of such a built-in recording medium include TOUCH MEMORY PROBE DS9092, and ADD ONLY MEMORY DS2505, (trade names, products of Dallas Semiconductor Corporation). In this case, because the recording medium is built into a connector which is united to the NOx sensor, a one-to-one relation is reliably established between data recorded on the recording medium and the NOx sensor. In other words, there are no incidents in which data concerning a certain NOx sensor is erroneously related to another NOx sensor.

Preferably, the NOx-concentration detecting apparatus further comprises standard-characteristic storage means for storing predetermined standard characteristics representing correlations among the first pumping current value, the second pumping current value and the concentration of NOx in the measurement gas. The recording means contains correction data for making the previously measured characteristics of the NOx sensor equal to the standard characteristics, which characteristics represent correlations among the first pumping current value, the second pumping current value and the concentration of NOx in the measurement gas. The NOx-concentration detecting means detects the first pumping current value and the second pumping current value, corrects the detected values based on the correction data stored in the recording means, and determines the concentration of NOx in the measurement gas using the standard characteristics stored in the standard-characteristic storage means.

In this case, the NOx-concentration detecting means detects the first pumping current value and the second pumping current value, corrects the detected values based on the correction data stored in the recording means, and determines the concentration of NOx in the measurement gas using the standard characteristics stored in the standard-characteristic storage means, namely, the standard characteristics representing correlations among the first pumping current value, the second pumping current value and the concentration of NOx in the measurement gas.

The correction data are used for making the previously measured characteristics of the NOx sensor equal to the standard characteristics, which characteristics represent correlations among the first pumping current value, the second pumping current value and the concentration of NOx in the measurement gas. The standard characteristics are characteristics of a specific sensor serving as a standard sensor. The previously measured sensor characteristics are those actually measured for each NOx sensor because the above-mentioned characteristics vary among individual NOx sensors.

Accordingly, when the concentration of NOx in the same measurement gas is measured using different NOx sensors, any of the NOx sensors can provide an accurate measurement because variations in measurement among the sensors are corrected by the correction data. The above-mentioned characteristics peculiar to each NOx sensor do not need to be stored. That is, storage may be limited to the standard characteristics and correction data, so that the storage capacity needed for storing such data is relatively small. Accordingly, the correction data can be stored on the recording means which is also used for recording the operating conditions of the NOx sensor.

On the other hand, the above second object of the present invention has been achieved by providing an NOx-concentration detecting apparatus comprising an NOx sensor, pumping-current control means, and constant-voltage application means.

The NOx sensor of the above second aspect of the invention comprises a first measurement space and a second measurement space. The first measurement space comprises a first oxygen-pumping cell and an oxygen-concentration-measuring cell and communicates with a measurement gas via a first diffusion-controlling layer. Each of the first oxygen-pumping cell and the oxygen-concentration-measuring cell is formed by an oxygen-ion conductive solid electrolyte layer and porous electrodes disposed on opposite surfaces of the oxygen-ion conductive solid electrolyte layer. The second measurement space comprises a second oxygen-pumping cell and communicates with the first measurement space via a second diffusion-controlling layer. The second oxygen-pumping cell is formed by an oxygen-ion conductive solid electrolyte layer and porous electrodes disposed on opposite surfaces of the oxygen-ion conductive solid electrolyte layer.

The pumping-current control means controls the concentration of oxygen contained in the first measurement space at a constant level by pumping out oxygen from the first measurement space by means of the first oxygen-pumping cell such that an output voltage from the oxygen-concentration-measuring cell is maintained at a constant value.

The constant-voltage application means applies a constant voltage to the second oxygen-pumping cell in a direction (or polarity) such that oxygen is pumped out from the second measurement space.

The NOx-concentration detecting apparatus further comprises standard-characteristic storage means, correction data storage means and NOx-concentration detecting means.

The standard-characteristic storage means stores predetermined standard characteristics which represent correlations among the current flowing through the first oxygen-pumping cell when controlled by the pumping-current control means, current flowing through the second oxygen-pumping cell when a voltage is applied to the second oxygen-pumping cell by the constant-voltage application means, and the concentration of NOx in the measurement gas.

The correction data storage means stores correction data for making previously measured characteristics of the NOx sensor equal to the standard characteristics, which characteristics represent correlations among the first pumping current, the second pumping current and the concentration of NOx in the measurement gas.

The NOx-concentration detecting means detects the first pumping current and the second pumping current, corrects the detected current values based on the correction data stored in the correction data storage means, and determines the concentration of NOx in the measurement gas using the standard characteristics stored in the standard-characteristic storage means.

As in the case of the aforementioned conventional NOx-concentration detecting apparatus, the NOx-concentration detecting apparatus of the second aspect of the present invention determines the concentration of NOx in the measurement gas using an NOx sensor. Specifically, the pumping-current control means controls the concentration of oxygen contained in the first measurement space to a constant level. The constant-voltage application means applies a constant voltage to the second oxygen-pumping cell in a direction (polarity) such that oxygen is pumped out from the second measurement space. The NOx-concentration detecting means determines the concentration of NOx in the measurement gas based on the value of current which flows through the second oxygen-pumping cell as a result of applying a constant voltage to the second oxygen-pumping cell.

The NOx-concentration detecting means for use in the second aspect of the present invention detects the first pumping current and the second pumping current, corrects the detected current values based on correction data stored in the correction data storage means, and determines the concentration of NOx in the measurement gas using standard characteristics stored in the standard-characteristic storage means, namely, the standard characteristics representing correlations among the first pumping current, the second pumping current and the concentration of NOx in the measurement gas.

The correction data are used for making the previously measured characteristics of the NOx sensor equal to the standard characteristics, which characteristics represent correlations among the first pumping current value, the second pumping current value and the concentration of NOx in the measurement gas. The standard characteristics are characteristics of a specific sensor serving as a standard sensor. The previously measured sensor characteristics are those actually measured for each NOx sensor because the above-mentioned characteristics vary among individual NOx sensors.

Thus, according to the second aspect of the present invention, when the concentration of NOx in the same measurement gas is measured using different NOx sensors, any of the NOx sensors can provide an accurate measurement since variations in measurement among the sensors are corrected by the correction data. The above-mentioned characteristics peculiar to each NOx sensor need not be stored. That is, storage may be limited to the standard characteristics and correction data, so that the storage capacity needed for storing such data is relatively small. Accordingly, the NOx-concentration detecting apparatus of the second aspect of the present invention is advantageous in that the configuration can be simplified and the concentration of NOx can be determined at high resolution irrespective of the NOx sensor used in combination therewith.

The NOx-concentration detecting means usually determines the concentration of oxygen in the measurement gas based on the detected value of the first pumping current and on the relationship between the concentration of oxygen in the measurement gas and the first pumping current. From the thus-obtained concentration of oxygen, the NOx-concentration detecting means determines an offset current value (described below) based on the relationship between the concentration of oxygen in the measurement gas and the second pumping current. As for the concentration of NOx in the measurement gas, the NOx-concentration detecting means determines an NOx concentration corresponding to a value obtained by subtracting the thus-obtained offset current value from a detected value of the second pumping current.

The offset current value is the value of current flowing through the second oxygen-pumping cell when the NOx content of the measurement gas is zero. Specifically, the concentration of oxygen contained in the first measurement space is set at a low level such that application of the first pumping current to the first pumping cell does not decompose nitrogen oxides contained in the measurement gas contained in the first measurement space. Thus, even when the NOx content of the measurement gas is zero, the small amount of oxygen present in the first measurement space causes current to flow through the second oxygen-pumping cell. Because the current flow does not depend on the concentration of NOx, the value of the current is taken as an offset current value and subtracted from the second pumping current value.

Accordingly, preferably, the above-mentioned characteristics include at least a correlation between the concentration of oxygen in the measurement gas and the first pumping current, a correlation between the concentration of NOx in the measurement gas and the second pumping current, and a correlation between the concentration of oxygen in the measurement gas and the second pumping current (i.e., the offset current). These three correlations are used by the NOx-concentration detecting means to determine the concentration of NOx in the measurement gas as mentioned above, and have a significant effect on measurement accuracy.

Preferably, the above-mentioned correlation between the concentration of NOx in the measurement gas and the second pumping current includes a correlation between the concentration of oxygen in the measurement gas and the rate of change in the second pumping current relative to the concentration of NOx in the measurement gas. Because the correlation between the concentration of NOx in the measurement gas and the second pumping current is normally linear, the rate of change in the second pumping current relative to NOx concentration is substantially constant and is called the $I_{p2}$ gain. Because the $I_{p2}$ gain slightly varies depending on the concentration of oxygen in the measurement gas, the corresponding correction of the $I_{p2}$ gain further improves measurement accuracy.

Preferably, the above-mentioned characteristics include a correlation between the temperature of the NOx sensor and the second pumping current. Because the value of the second pumping current is sensitive to the temperature of the NOx sensor, measurement accuracy is further improved through correction of the second pumping current value for the temperature of the NOx sensor. Specifically, this is the temperature of the oxygen-concentration-measuring cell used to detect the concentration of oxygen in the first measurement space. Preferably, the temperature of the NOx sensor is controlled to a constant level. Even in this case, such control may fail to follow a change in the temperature of the measurement gas with a resultant variation in the temperature of the NOx sensor. Therefore, the second pumping current value is preferably corrected for the temperature of the NOx sensor.

Preferably, the NOx sensor and the correction data storage means are removably mounted. In this case, when the NOx sensor must be replaced due to a failure or the like, the NOx sensor is replaced with a new one. The correction data storage means is also replaced with one containing correction data corresponding to the new NOx sensor, thereby enabling use of the NOx-concentration detecting apparatus. The NOx sensor may be made removable by means of, for example, a connector. Examples of the correction data storage means include flexible disks (floppy disks and the like), optical disks, magneto-optical disks, and like recording media. Such a recording medium may be removably mounted in a drive. Because a recording medium contains data concerning a specific NOx sensor, the recording medium preferably accompanies the NOx sensor.

Preferably, the correction data storage means is a substantially button-like recording medium adapted to be removable via a mount. Examples of such a recording medium include TOUCH MEMORY BUTTON, DS1995, (trade name, product of Dallas Semiconductor Corporation). Examples of such a mount include TOUCH MEMORY MOUNT PRODUCT, DS9093x, (trade name, product of Dallas Semiconductor Corporation). In this case, the recording medium is smaller, and thus can more readily accompany a corresponding NOx sensor.

When the NOx-concentration detecting apparatus of the present invention includes a connector which is united to the NOx sensor and establishes an electrical connection between the NOx sensor and the NOx-concentration detecting means, the correction data storage means is preferably built into the connector. Examples of such a built-in recording medium include TOUCH MEMORY PROBE DS9092, and ADD ONLY MEMORY DS2505, (trade names, products of Dallas Semiconductor Corporation). In this case, because the recording medium is built into a connector which is united to a NOx sensor, the recording medium accompanies the corresponding NOx sensor without fail. Such an NOx-concentration detecting apparatus is suitable, for example, for use on board an automobile.

A recording medium for use in the NOx-concentration detecting apparatus of the present invention and which contains the above-mentioned various correction data is useful for determining NOx concentration at high resolution using any sensor. Because the recording medium contains data concerning a specific NOx sensor, the recording medium preferably accompanies the NOx sensor.

DESCRIPTION OF THE PREFERRED EMBODIMENTS

Figure 1:
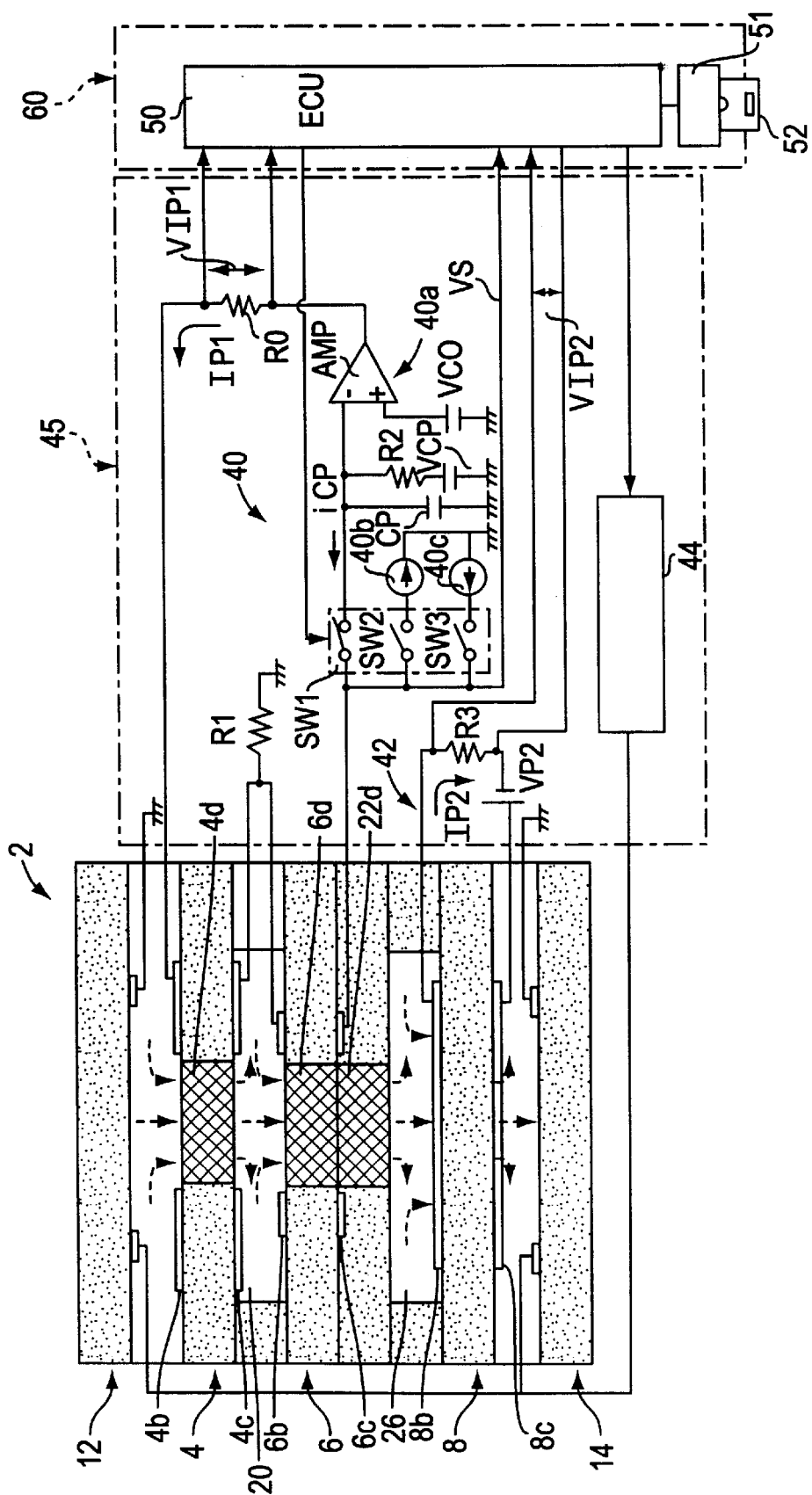
FIG. 1 is a schematic diagram showing the entire internal configuration of an NOx-concentration detecting apparatus according to a first embodiment of the present invention.
Figure 2:
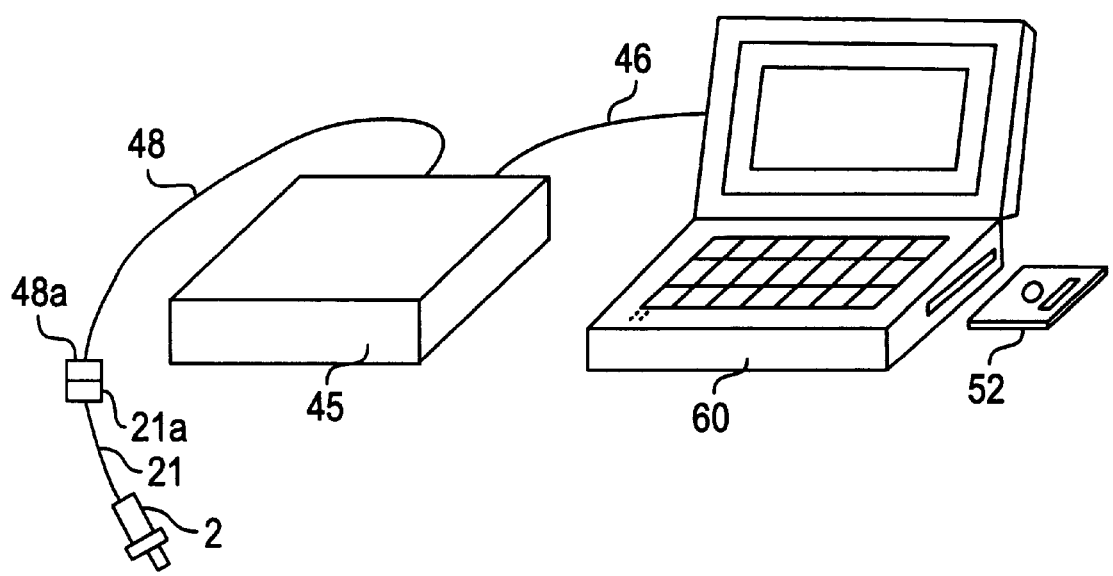
FIG. 2 is a schematic view showing the entire external configuration of the NOx-concentration detecting apparatus of the first embodiment.
Figure 3:
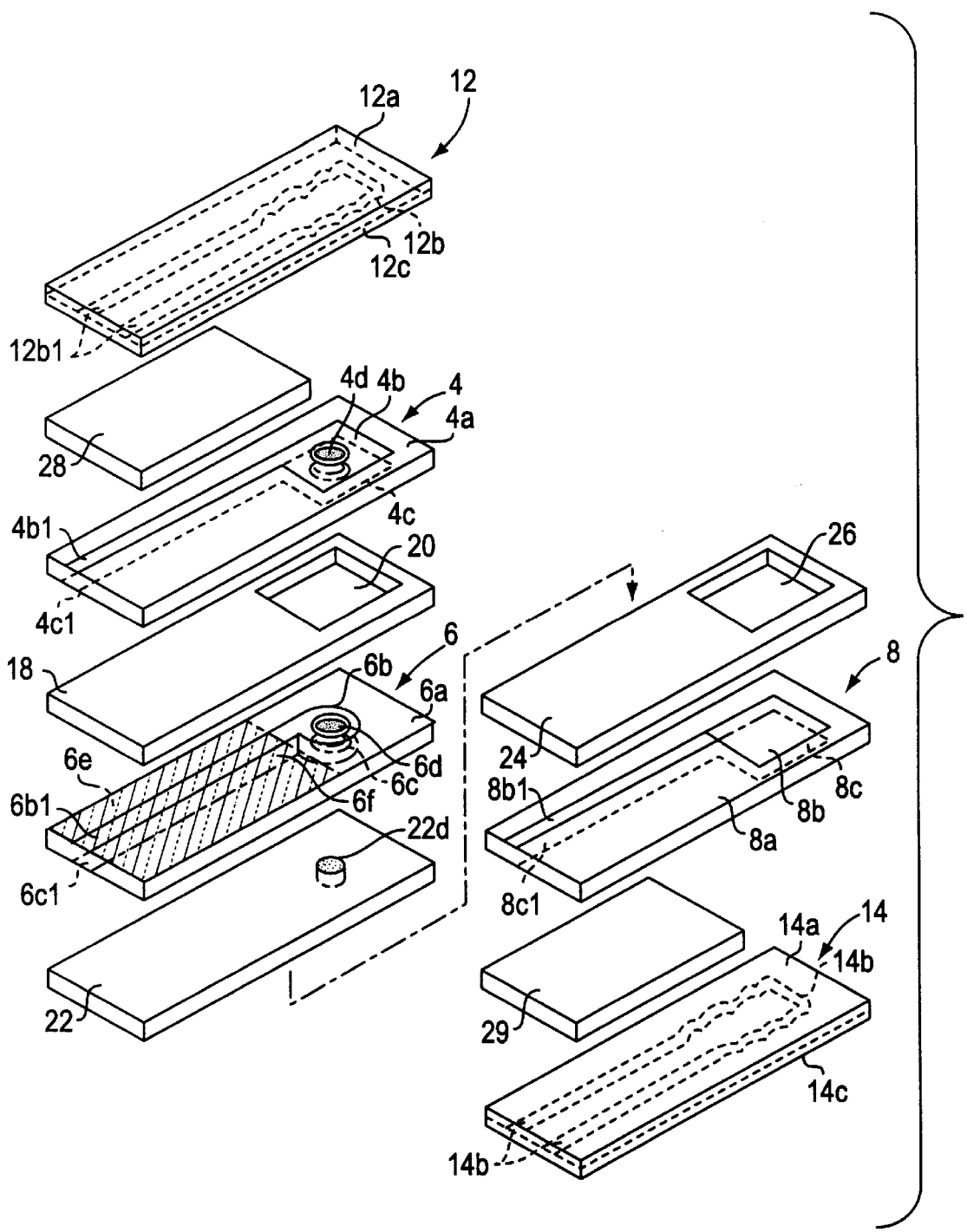
FIG. 3 is an exploded perspective view showing the structure of an NOx sensor.

Embodiments of the present invention will now be described in further detail with reference to the drawings which should not be construed as limiting the invention in any way.
First Embodiment:

FIG. 1 shows the entire internal configuration of an NOx-concentration detecting apparatus according to a first embodiment of the present invention. FIG. 2 schematically shows the external configuration of the NOx-concentration detecting apparatus. FIG. 3 is an exploded perspective view of an NOx sensor used in the NOx-concentration detecting apparatus.

As shown in FIG. 1, the NOx-concentration detecting apparatus includes an NOx sensor 2; a drive circuit 40 for applying current to a first oxygen-pumping cell (hereinafter referred to as a first pumping cell) 4 and an oxygen-concentration-measuring cell (hereinafter referred to as a Vs cell) 6 of the NOx sensor 2 and for switching one current application path to the other; a sensing circuit 42 for detecting current (hereinafter referred to as a s second pumping current) $I_{P2}$ which flows to a second oxygen-pumping cell (hereinafter referred to as a second pumping cell) 8 of the NOx sensor 2 when a constant voltage is applied to the second pumping cell 8; a heater-energizing circuit 44 for heating the cells 4, 6 and 8 by applying current to a pair of heaters 12 and 14 of the NOx sensor 2; and an electronic control unit (hereinafter referred to as an ECU) 50, which includes a microcomputer, for driving and controlling the drive circuit 40 and the heater-energizing circuit 44, and for calculating the concentration of NOx in a measurement gas based on a detection signal $V_{IP2}$ issued from the sensing circuit 42.

The drive circuit 40, the sensing circuit 42 and the heater-energizing circuit 44 are contained in a control box 45 shown in FIG. 2. The ECU 50 may be implemented in the form of a personal computer 60 which includes a floppy disk drive capable of reading recorded data from a floppy disk 52 (serving as a recording means of the invention). The control box 45 and the personal computer 60 are electrically connected by means of a cable 46. The control box 45 has a connection cable 48 which, in turn, has a connector 48a at its end. The NOx sensor 2 has a connection cable 21 which, in turn, has a connector 21a at its end. The connectors 21a and 48a are connected to establish an electrical connection. Accordingly, by disconnecting the connectors 21a and 48a from each other, the NOx sensor 2 is readily replaced.

As shown in FIG. 3, in the NOx sensor 2, The first pumping cell 4 includes a sheet-like solid electrolyte layer 4a and rectangular porous electrodes 4b and 4c formed on both sides of the solid electrolyte layer 4a. Lead portions 4b1 and 4c1 extend from the porous electrodes 4b and 4c, respectively. Furthermore, a round hole is formed in the solid electrolyte layer 4a in such manner as to penetrate the porous electrodes 4b and 4c at their central portions. The thus-formed round hole is filled with a porous filler to thereby form a diffusion-controlling layer 4d.

The Vs cell 6 includes a sheet-like solid electrolyte layer 6a similar to the solid electrolyte layer 4a of the first pumping cell 4 and circular porous electrodes 6b and 6c formed on opposing sides of the solid electrolyte layer 6a. Lead portions 6b1 and 6c1 extend from the porous electrodes 6b and 6c, respectively. Furthermore, a round hole is formed in the solid electrolyte layer 6a in such manner as to penetrate the porous electrodes 6b and 6c at their central portions. The thus-formed round hole is filled with a porous filler to thereby form a diffusion-controlling layer 6d.

The porous electrodes 4b and 4c of the first pumping cell 4 and the porous electrodes 6b and 6c of the Vs cell 6 are located on the solid electrolyte layers 4a and 6a, respectively, such that their centers are aligned with each other. Accordingly, when the first pumping cell 4 and the Vs cell 6 are arranged in layers, the diffusion-controlling layers 4d and 6d face each other. The circular porous electrodes 6b and 6c of the Vs cell 6 are arranged around the diffusion-controlling layer 6d and have a size smaller than that of the rectangular porous electrodes 4b and 4c of the first pumping cell 4. An insulation film formed of alumina or the like is formed on both surfaces of the Vs cell 6 so as to cover the lead portions 6b1 and 6c1 from the outside in order to prevent current leakage from the lead portions 6b1 and 6c1. Furthermore, a leakage resistance portion 6f is formed between the lead portions 6b1 and 6c1 in order to leak part of pumped-out oxygen from the side of the porous electrode 6c to the side of the porous electrode 6b.

The first pumping cell 4 and the Vs cell 6 are arranged in layers with a solid electrolyte layer 18 interposed therebetween. The solid electrolyte layer 18 has the same shape as that of the solid electrolyte layers 4a and 6a. The solid electrolyte layer 18 has a rectangular hole formed therein in a position corresponding to the porous electrodes 4c and 6b and has a size greater than that of the porous electrode 4c. The thus-formed rectangular hole serves as a first measurement space 20.

Also, a solid electrolyte layer 22, which has the same shape as that of the solid electrolyte layers 4a and 6a, is placed on the Vs cell 6 on the side of the porous electrode 6c. The solid electrolyte layer 22 has a round hole formed therein in a position corresponding to the diffusion-controlling layer 6d of the Vs cell 6 and having the same size as that of the diffusion-controlling layer 6d. The thus-formed round hole is filled with a porous filler to thereby form a diffusion-controlling layer 22d.

As in the first pumping cell 4, the second pumping cell 8 includes a sheet-like solid electrolyte layer 8a and rectangular porous electrodes 8b and 8c formed on opposing sides of the solid electrolyte layer 8a. Lead portions 8b1 and 8c1 extend from the porous electrodes 8b and 8c, respectively. The second pumping cell 8 and the solid electrolyte layer 22 are arranged in layers with a solid electrolyte layer 24 interposed therebetween. The solid electrolyte layer 24 is formed in the same manner as the solid electrolyte layer 18. As a result, a rectangular hole formed in the solid electrolyte layer 24 serves as a second measurement space 26.

Heaters 12 and 14 are placed on opposite sides of the above-described laminate of the first pumping cell 4, the Vs cell 6 and the second pumping cell 8, namely, outside the first pumping cell 4 and the second pumping cell 8, respectively, such that a predetermined gap is formed between each of the heaters 12 and 14 and the laminate via spacers 28 and 29.

The heater 12 (14) includes heater substrates 12a and 12c (14a and 14c) having a shape similar to that of the solid electrolyte layers 4a, 6a, . . . , a heater wiring 12b (14b), and a lead portion 12b1 (14b1) extending from the heater wiring 12b (14b). The heater wiring 12b (14b) and the lead portion 12b1 (14b1) are interposed between the heater substrates 12a and 12c (14a and 14c). The spacer 28 (29) is interposed between the heater 12 (14) and the first pumping cell 4 (second pumping cell 8) so that the heater 12 (14) faces the porous electrode 4b (8c) of the first pumping cell 4 (second pumping cell 8) with a gap formed therebetween.

Typical examples of the solid electrolyte useful for forming the solid electrolyte layers 4a, 6a, . . . include a solid solution of zirconia and yttria and a solid solution of zirconia and calcia. Other examples of such a solid electrolyte include a solid solution of hafnia, a solid solution of a perovskite oxide, and a solid solution of a trivalent metal oxide. The porous electrodes provided on the surfaces of the solid electrolyte layers 4a, 6a and 8a are preferably formed of platinum or rhodium having a catalytic function or alloys thereof. Known methods of forming such a porous electrode include a thick-film forming method and a thermal spraying method. The thick-film forming method includes the steps of: mixing platinum powder and powder of the same material as that of the solid electrolyte layers to obtain a paste; screen-printing the paste onto a solid electrolyte layer; and sintering the solid electrolyte layer. The diffusion-controlling layers 4d, 6d and 22d are preferably formed of ceramics having fine through-holes or porous ceramics.

The heater wirings 12b and 14b of the heaters 12 and 14, respectively, are preferably formed of a composite material of ceramics and platinum or a platinum alloy. The lead portions 12b1 and 14b1 are preferably formed of platinum or a platinum alloy in order to reduce electric loss therein by reducing their resistance. The heater substrates 12a, 12b, 14a and 14c and the spacers 28 and 29 may be formed of alumina, spinel, forsterite, steatite, zirconia, or the like.

Particularly preferably, the heater substrates and spacers are formed of zirconia because the heaters and pumping cells can be concurrently united by sintering to thereby facilitate the manufacture of the NOx sensor 2. In this case, an insulation layer (formed of alumina or the like) is interposed between the heater substrate 12a (12c) and the heater wiring 12b including the lead portion 12b1, and between the heater substrate 14a (14c) and the heater wiring 14b including the lead portion 14b1.

When the heater substrates are formed of alumina, the spacers are preferably formed of a porous material in order to prevent cracking which would otherwise occur during sintering of the heater substrates and the pumping cells due to differences in their coefficients of contraction or thermal expansion. Alternatively, the heaters and the pumping cells may be sintered separately, and they may then be bonded using cement or a like inorganic material serving as both a spacer and a bonding material.

As shown in FIG. 1, the porous electrode 4c of the first pumping cell 4 and the porous electrode 6b of the Vs cell 6, both of which are located on the side of the first measurement space 20, are grounded via a resistor R1. The other porous electrodes 4b and 6c are connected to the drive circuit 40.

The drive circuit 40 includes a control section 40a which, in turn, includes a resistor R2 and a differential amplifier AMP. A constant voltage $V_{CP}$ is applied to one end of the resistor R2, and the other end of the resistor R2 is connected to the porous electrode 6c of the Vs cell 6 via a switch SW1. The negative input terminal of the differential amplifier AMP is connected to the porous electrode 6c of the Vs cell 6 via the switch SW1 and to one end of a capacitor Cp. A reference voltage $V_{C0}$ is applied to the positive input terminal of the differential amplifier AMP. The output terminal of the differential amplifier AMP is connected to the porous electrode 4b of the first pumping cell 4 via a resister R0. The other end of the capacitor Cp is grounded.

When the switch SW1 is in the ON state, the control section 40a operates in the following manner.

First, a constant small current $i_{CP}$ is supplied to the Vs cell 6 via the resistor R2 to thereby pump out oxygen from the first measurement space 20 into the porous electrode 6c of the Vs cell 6. Because the porous electrode 6c is blocked by the solid electrolyte layer 22 and communicates with the porous electrode 6b via the leakage resistance portion 6f, the concentration of oxygen contained in the blocked space of the porous electrode 6c is maintained at a constant level by applying a small current $i_{CP}$ to the Vs cell 6. Thus, the blocked space serves as an internal reference oxygen source.

When the porous electrode 6c of the Vs cell serves as an internal reference oxygen source, an electromotive force is generated in the Vs cell 6 in accordance with the difference in oxygen concentration between the first measurement space 20 and the internal reference oxygen source. As a result, a voltage Vs generated on the side of the porous electrode 6c corresponds to the concentration of oxygen contained in the first measurement space 20. Because the voltage Vs is input to the differential amplifier AMP, the differential amplifier AMP outputs a voltage in accordance with the deviation of the input voltage from the reference voltage $V_{C0}$ ($V_{C0}$—input voltage). The output voltage is applied to the porous electrode 4b of the first pumping cell 4 via the resistor R0.

As a result, a current $I_{P1}$ (hereinafter referred to as a first pumping current $I_{P1}$) flows through the first pumping cell 4. By controlling the first pumping current $I_{P1}$, a constant electromotive force is generated in Vs cell 6 (in other words, the concentration of oxygen contained in the first measurement space 20 becomes constant).

That is, the control section 40a serves as the pumping-current control means of the invention, and controls the amount of oxygen pumped out of the first measurement space 20. Thus, the concentration of oxygen contained in a measurement gas which has entered the first measurement space 20 via the diffusion-controlling layer 4d is maintained constant.

The thus-controlled concentration of oxygen contained in the first measurement space 20 is set such that only a small amount of oxygen (e.g., 100 ppm) is present, thereby preventing decomposition of an NOx component of the measurement gas contained in the first measurement space 20 due to applying a first pumping current $I_{P1}$ to the first pumping cell 4. The reference voltage $V_{C0}$ for determining this concentration of oxygen is set at 100 mV to 200 mV. The resistor R0 disposed between the output terminal of the differential amplifier AMP and the porous electrode 4b is adapted to detect the first pumping current $I_{P1}$. A voltage $V_{IP1}$ generated across the resistor R0 is input to the ECU 50 as a detection signal corresponding to the first pumping current $I_{P1}$.

The drive circuit 40 further includes a constant-current circuit 40b and a constant-current circuit 40c. The constant-current circuit 40b is connected to the porous electrode 6c of the Vs cell 6 via a switch SW2 and causes a constant current to flow between the porous electrodes 6b and 6c in a direction opposite the flowing direction of the small current $i_{CP}$. The constant-current circuit 40c is connected to the porous electrode 6c of the Vs cell 6 via a switch SW3 and causes a constant current to flow between the porous electrodes 6b and 6c in the same direction as the flowing direction of the small current $i_{CP}$.

The constant-current circuits 40b and 40c are adapted to detect the internal resistance $R_{VS}$ of the Vs cell 6. In order for the ECU 50 to detect the internal resistance $R_{VS}$ of the Vs cell 6 by supplying a constant current to the Vs cell 6, the voltage Vs built on the side of the porous electrode 6c is input to the ECU 50. The constant-current circuits 40b and 40c supply a constant current of the same value in opposite directions. The value of the constant current is greater than that of the small current $i_{CP}$, which is supplied to the Vs cell 6 via the resistor R2.

The switches SW1, SW2 and SW3 provided between the porous electrode 6c of the Vs cell 6 and the control section 40a and the constant-current circuits 40b and 40c, respectively, are turned ON or OFF in accordance with a control signal issued by the ECU 50. In the normal mode where the NOx concentration is to be detected via the control section 40a, only switch SW1 is turned ON. When the internal resistance $R_{VS}$ of the Vs cell 6 alone is to be detected, switch SW1 is turned OFF, and switches SW2 and SW3 are sequentially turned ON in this order.

A constant voltage VP2 is applied between the porous electrodes 8b and 8c of the second pumping cell 8 of the NOx sensor 2 via a resistor R3, which is a component of the sensing circuit 42 and serves as the constant-voltage application means of the invention. The constant voltage VP2 is applied to the second pumping cell 8 in a direction (polarity) such that the porous electrodes 8c and 8b assume positive and negative polarities, respectively. As a result, current flows from the porous electrode 8c to the porous electrode 8b to thereby pump out oxygen from the second measurement space 26. The constant voltage VP2 is set at a voltage, for example 450 mV, such that the NOx component contained in the measurement gas flowing from the first measurement space 20 to the second measurement space 26 via the diffusion-controlling layers 6d and 22d can be decomposed, to thereby pump out an oxygen component from the measurement gas.

The resistor R3 is adapted to convert the second pumping current $I_{P2}$ flowing through the second pumping cell 8 as a result of application of the constant voltage VP2, to a voltage $VP_{IP2}$, and adapted to input the voltage $V_{IP2}$ to the ECU 50 as a detection signal corresponding to the second pumping current $I_{P2}$.

In the NOx-concentration detecting apparatus having the above-described configuration, by turning switch SW1 ON and switches SW2 and SW3 OFF, the control section 40a can control the concentration of oxygen contained in the measurement gas which has entered the first measurement space 20 via the diffusion-controlling layer 4d (first diffusion-controlling layer 4d), to a constant level. The measurement gas controlled at a constant oxygen concentration flows from the first measurement space 20 to the second measurement space 26 via the diffusion-controlling layers 6d and 22d (second diffusion-controlling layers 6d and 22d). Accordingly, the second pumping current $I_{P2}$ flowing through the second pumping cell 8 varies in accordance with the NOx concentration. Thus, by reading the detection signal $V_{IP2}$ corresponding to the second pumping current $I_{P2}$, and carrying out a predetermined computation based on the read signal, the ECU 50 can determine the concentration of NOx in the measurement gas from the detection signal $V_{IP2}$ (in other words, the second pumping current $I_{P2}$). That is, the ECU 50 serves as the NOx-concentration detecting means of the invention.

In order to secure a constant degree of accuracy in detecting the NOx concentration, the temperature of the cells 4, 6 and 8, particularly the temperature of the Vs cell 6 adapted to detect the concentration of oxygen contained in the first measurement space 20, must be controlled at a constant value. Thus, the amount of current applied to the heaters 12 and 14 by the heater-energizing circuit 44 must be controlled such that the temperature of the Vs cell 6 achieves a target value. To attain this end, in the present embodiment, the ECU 50 detects the internal resistance $R_{VS}$ of the Vs cell 6 by appropriately setting the switches SW1, SW2 and SW3 to the ON or OFF state and controlling the amount of current supplied from the heater-energizing circuit 44 to the heaters 12 and 14 such that the detected internal resistance $R_{VS}$ becomes constant (that is, the temperature of the Vs cell 6 achieves a target value).

Figure 4:
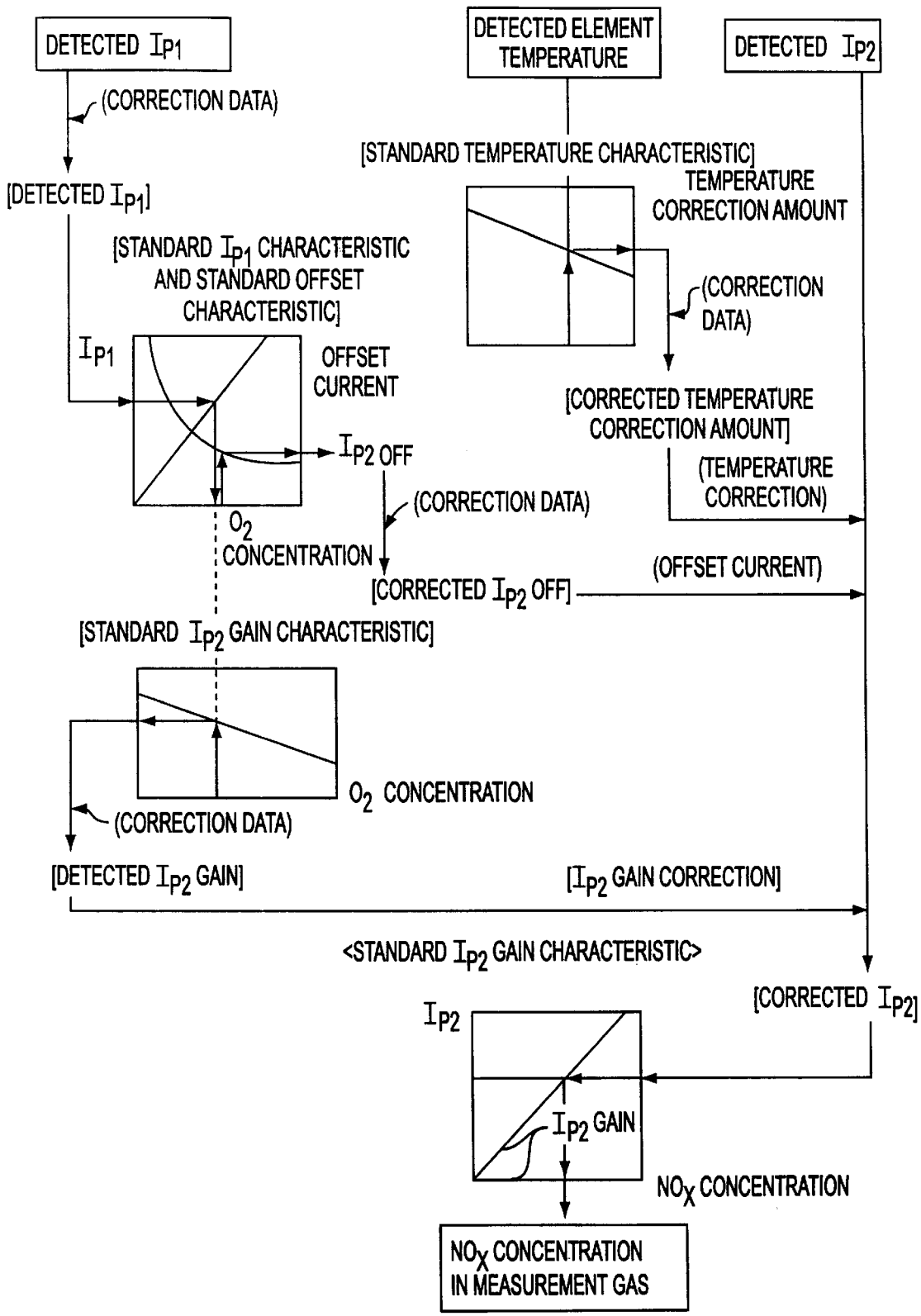
FIG. 4 is a diagram showing the procedure for determining NOx concentration.

Next, the procedure of determining the concentration of NOx in the measurement gas in the NOx-concentration detecting apparatus of the present embodiment is described as follows. FIG. 4 shows the procedure of determining the NOx concentration.

First, a standard NOx sensor 2 is selected. By using a standard NOx sensor 2 and a test gas which does not contain oxygen and which serves as a measurement gas, the characteristic of the second pumping current $I_{P2}$ relative to the NOx concentration (hereinafter referred to as the $I_{P2}$ characteristic) is measured. The thus-measured $I_{P2}$ characteristic is stored in an unillustrated ROM of the ECU 50 as the standard $I_{P2}$ characteristic (see FIG. 4). The ECU 50 detects the second pumping current $I_{P2}$, and determines the concentration of NOx in the measurement gas from the detected second pumping current $I_{P2}$ and the standard $I_{P2}$ characteristics. The measurement gas which does not contain oxygen shows a substantially constant rate of change in the second pumping current $I_{P2}$ relative to the NOx concentration. This constant rate of change is called the $I_{P2}$ gain.

In the present embodiment, through the above-mentioned pumping-current control performed by the drive circuit 40, the concentration of oxygen in the first measurement space 20 is controlled to a low level so as not to decompose an NOx component of the measurement gas contained in the first measurement space 20. Thus, not only NOx contained in the measurement gas but also oxygen remaining in the first measurement space 20 flows into the second measurement space 26. Accordingly, the second pumping current $I_{P2}$ not only varies in accordance with the concentration of NOx in the measurement gas but is also influenced by the concentration of oxygen in the measurement gas. That is, even when the measurement gas does not contain any NOx component, the second pumping current $I_{P2}$ varies in relation to the concentration of oxygen in the measurement gas. To cope with this phenomenon, by using the standard NOx sensor 2 and a test gas which does not contain any NOx component as a measurement gas, the characteristic of the second pumping current $I_{P2}$ relative to oxygen concentration (hereinafter, this second pumping current $I_{P2}$ is referred to as the offset current $I_{P2OFF}$, and this characteristic is referred to as the offset characteristic) is measured in advance. The thus-measured offset characteristic is stored in an unillustrated ROM of the ECU 50 as the standard offset characteristic (see FIG. 4). Based on the aforementioned $I_{P2}$ characteristic, the NOx concentration is determined from a value obtained by subtracting from the detected second pumping current $I_{P2}$ the offset current $I_{P2OFF}$ corresponding to the oxygen concentration at the time of the detection. Correction for the offset current $I_{P2OFF}$ is called correction for offset.

In order to detect the offset current $I_{P2OFF}$, the concentration of oxygen in the measurement gas must be detected. This oxygen concentration can be obtained from the first pumping current $I_{P1}$. However, during pumping-current control, the first pumping current $I_{P1}$ varies depending on the concentration of oxygen in the measurement gas. To cope with this phenomenon, by using the standard NOx sensor 2 and a test gas which does not contain any NOx component as a measurement gas, the characteristic of the first pumping current relative to the oxygen concentration (hereinafter referred to as the $I_{P1}$ characteristic) is measured in advance. The thus-measured $I_{P1}$ characteristic is stored in an unillustrated ROM of the ECU 50 as the standard $I_{P1}$ characteristic (see FIG. 4). The oxygen concentration is determined from the detected first pumping current $I_{P1}$ and the standard $I_{P1}$ characteristic. The offset current $I_{P2OFF}$ is obtained from the thus-determined oxygen concentration as described above. When the NOx concentration is to be determined from the detected second pumping current $I_{P2}$, the detected second pumping current $I_{P2}$ is preferably corrected for the temperature of the NOx sensor 2 (hereinafter referred to as the element temperature) because the second pumping current $I_{P2}$ varies with the element temperature. In this regard, in the present embodiment, the internal resistance $R_{VS}$ of the Vs cell 6 is detected, and the amount of current supplied to the heaters 12 and 14 is controlled such that the detected internal resistance $R_{VS}$ becomes a predetermined value (in other words, the element temperature achieves a predetermined target value). However, upon an abrupt change in the temperature of the measurement gas, the temperature control fails to follow the temperature change of the measurement gas. As a result, the temperature change of the measurement gas may cause a change in the element temperature. In this case, the second pumping current $I_{P2}$ varies with the element temperature. To cope with this phenomenon, by using the standard NOx sensor, the characteristic of the second pumping current $I_{P2}$ relative to the element temperature (hereinafter referred to as the temperature characteristic) is measured in advance. The thus-measured temperature characteristic is stored in an unillustrated ROM of the ECU 50 as the standard temperature characteristic (see FIG. 4). Based on the standard temperature characteristic, an amount of correction for temperature is obtained from the element temperature which, in turn, is obtained from the internal resistance $R_{VS}$. By using the thus-obtained amount of correction for temperature, the detected second pumping current $I_{P2}$ is corrected for temperature.

Also, when the NOx concentration is to be determined, the standard $I_{P2}$ characteristic is preferably corrected in accordance with the concentration of oxygen in the measurement gas because the $I_{P2}$ gain varies with the oxygen concentration. In the present embodiment, by using the standard NOx sensor 2, the $I_{P2}$ gain at a certain oxygen concentration (for example, zero) and the $I_{P2}$ gain at another oxygen concentration are measured in advance. Based on the measured values of the $I_{P2}$ gain, the linear-function-like characteristic of the $I_{P2}$ gain relative to the oxygen concentration (hereinafter referred to as the $I_{P2}$ gain characteristic) is calculated. The thus-calculated $I_{P2}$ gain characteristic is stored in an unillustrated ROM of the ECU 50 as the standard $I_{P2}$ gain characteristic (see FIG. 4). Based on the standard $I_{P2}$ gain characteristic, an amount of correction of the $I_{P2}$ gain is obtained from the oxygen concentration which, in turn, is obtained from the first pumping current $I_{P1}$. By using the thus-obtained amount of correction of the $I_{P2}$ gain, the detected second pumping current $I_{P2}$ is corrected accordingly.

The above-mentioned ROM serves as the standard-characteristic storage means of the present invention.

The above-mentioned $I_{P1}$ characteristic, offset characteristic, temperature characteristic, $I_{P2}$ gain characteristic differ slightly among individual NOx sensors 2. Thus, if NOx concentration is determined using the above-mentioned standard characteristics, a satisfactory degree of measurement accuracy is not obtained among various NOx sensors 2. Thus, according to the present embodiment, these characteristics are previously measured for each of the NOx sensors 2, and corresponding correction data ($I_{P1}$ characteristic correction data, offset characteristic correction data, temperature characteristic correction data and $I_{P2}$ gain characteristic correction data) are created such that the previously measured characteristics become equal to the above-mentioned respective standard characteristics. The thus-created correction data are stored on the floppy disk 52, which accompanies the relevant NOx sensor 2.

Figure 5A:
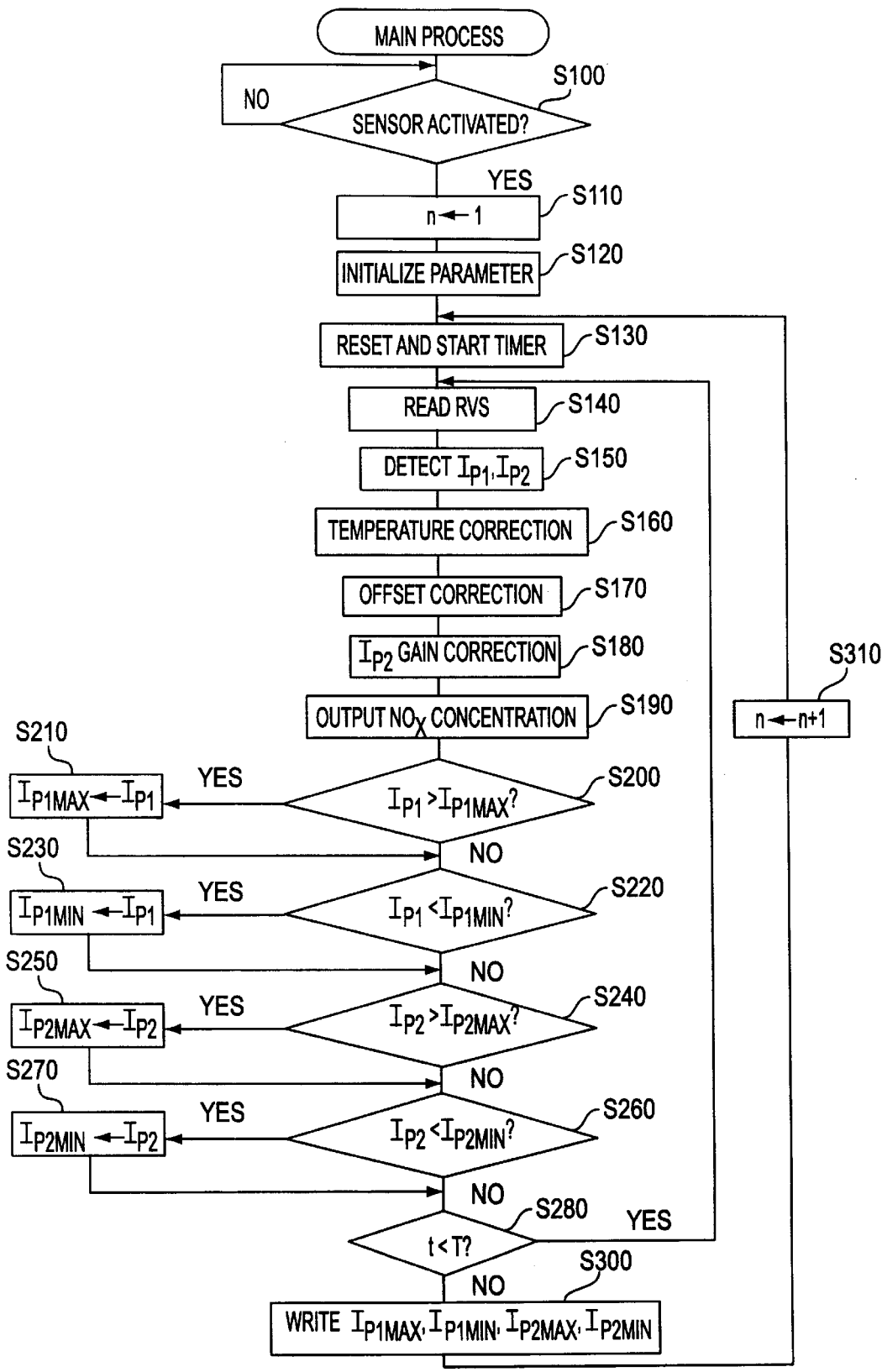
FIG. 5A is a flowchart showing a first main process which is repeatedly executed by an ECU.

Next, a main process executed by the ECU 50 of the NOx-concentration detecting apparatus will be described with reference to FIGS. 4 and 5A. FIG. 5A shows a flowchart of a first main process for determining NOx concentration and for recording operating conditions.

According to a first main process, record number n is set at 1, the maximum and minimum first pumping currents $I_{P1max}$ and $I_{P1min}$, respectively, and the maximum and minimum second pumping currents $I_{P2max}$ and $I_{P2min}$, respectively, are initialized to respective initial values, and then a timer is started. Then, an element temperature and first and second pumping currents $I_{P1}$ and $I_{P2}$, respectively, are detected. Based on the detected values, the NOx concentration is determined. Subsequently, if the detected $I_{P1}$ ($I_{P2}$) is greater than the initial $I_{P1max}$ ($I_{P2max}$) or smaller than the initial $I_{P1max}$ ($I_{P2max}$), the detected $I_{P1}$ ($I_{P2}$) will become a new $I_{P1max}$ ($I_{P2max}$) or $I_{P1min}$ ($I_{P2min}$) After the elapse of a predetermined periodic time T, $I_{P1max}$, $I_{P1min}$, $I_{P2max}$, and $I_{P2min}$ are associated with the current record number n and written onto a floppy disk.

Subsequent to starting the NOx-concentration detecting apparatus, in step S100 of the main process as shown in FIG. 5A, an activation judgment process for the NOx sensor 2 is executed. Specifically, a judgment is made whether or not to activate the NOx sensor 2 by applying current to the heaters 12 and 14. If the NOx sensor 2 is not activated, the processing is looped until the NOx sensor 2 is activated.

In the activation judgment process, for example, a determination is made as to whether or not the internal resistance $R_{VS}$ of the Vs cell 6 has dropped to or below a predetermined activation judgment value. The internal resistance $R_{VS}$ of the Vs cell 6 is reduced as the activation of the Vs cell 6 progresses with increasing element temperature. Thus, in step S100, after starting the supply of current to the heaters 12 and 14, a determination is made as to whether or not the internal resistance $R_{VS}$ of the Vs cell 6 has dropped to or below the activation judgment value, thereby judging whether or not the element temperature has reached a predetermined activation temperature.

Immediately after the NOx-concentration detecting apparatus is started, an unillustrated initialization process turns switch SW1 in the drive circuit 40 ON and turns switches SW2 and SW3 in the drive circuit 40 OFF. However, operation of the differential amplifier AMP in the drive circuit 40 is suspended until it is determined in the activation judgment process in step S100 that the temperature of the NOx sensor 2 has risen to near the activation temperature.

Next, when the NOx sensor 2 is judged active in step S100, processing proceeds to step S110, in which the record number n is set to 1. In subsequent step S120, the parameters to be recorded are initialized, i.e., set at their respective initial values. In the present embodiment, the parameters to be recorded are the maximum and minimum first pumping currents $I_{P1max}$ and $I_{P1min}$, respectively, and the maximum and minimum second pumping currents $I_{P2max}$ and $I_{P2min}$, respectively, and these parameters are set at respective initial values. These initial values are temporarily stored in an unillustrated RAM (temporary storage means) of the ECU 50. The maximum first pumping current $I_{P1max}$ and the maximum second pumping current $I_{P2max}$ are initialized to values smaller than those normally assumed by the first pumping current $I_{P1}$ and the second pumping current $I_{P2}$. The minimum first pumping current $I_{P1min}$ and the minimum second pumping current $I_{P2min}$ are initialized to values larger than those normally assumed by the first pumping current $I_{P1}$ and the second pumping current $I_{P2}$.

In step S130, the timer is reset, and then the measurement is started. As a result, the measurement of working time of the NOx sensor is started. Then, processing proceeds to step S140. In step S140, the internal resistance $R_{VS}$ of the Vs cell 6 is read, and the read internal resistance $R_{VS}$ is converted into the element temperature of the Vs cell 6. In step S150, the detection signal $V_{IP1}$ issued from the resistor R0 of the drive circuit 40 is read to thereby detect the first pumping current $I_{P1}$. Also, the detection signal $V_{IP2}$ issued from the resistor R3 of the sensing circuit 42 is read to thereby detect the second pumping current $I_{P2}$.

In step S160, based on the element temperature which was read in step S140, a correction amount for temperature is calculated for the second pumping current $I_{P2}$. Then, based on the thus-obtained temperature correction amount, the second pumping current $I_{P2}$ is corrected for temperature. Specifically, in order to accurately determine the NOx concentration from the second pumping current $I_{P2}$ even upon an abrupt change in the temperature of the measurement gas, a temperature correction amount of the Vs cell 6, i.e., for the element temperature, is obtained based on the standard temperature characteristic (see FIG. 4) stored in an unillustrated ROM. The thus-obtained temperature correction amount is corrected based on the temperature characteristic correction data read from the floppy disk 52 to obtain a corrected temperature correction amount. By using the corrected temperature correction amount, a correction for the temperature measurement is carried out.

After the above correction for temperature, processing proceeds to step S170, in which the second pumping current $I_{P2}$ is corrected for offset. Specifically, the $I_{P1}$ characteristic correction data is read from the floppy disk 52, and the first pumping current $I_{P1}$ is corrected based on the read $I_{P1}$ characteristic correction data to obtain the corrected first pumping current $I_{P1}$. The concentration of oxygen in the measurement gas is obtained from the corrected first pumping current $I_{P1}$ by using the standard $I_{P1}$ characteristic (see FIG. 4). The offset current $I_{P2OFF}$ is obtained from the thus-obtained oxygen concentration by using the standard offset characteristic (see FIG. 4). The thus-obtained offset current $I_{P2OFF}$ is corrected based on the offset characteristic correction data read from the floppy disk 52 to obtain the corrected offset current $I_{P2OFF}$. By using the corrected offset current $I_{P2OFF}$, the second pumping current $I_{P2}$ corrected for temperature is corrected for offset.

In step S180, the second pumping current $I_{P2}$ is corrected for $I_{P2}$ gain. Specifically, by using the standard $I_{P2}$ gain characteristic (see FIG. 4), the $I_{P2}$ gain is obtained from the oxygen concentration which, in turn, was obtained from the first pumping current $I_{P1}$. The thus-obtained $I_{P2}$ gain is corrected based on the $I_{P2}$ gain correction data read from the floppy disk 52 to obtain a corrected $I_{P2}$ gain. By using the corrected $I_{P2}$ gain, an $I_{P2}$ gain correction coefficient is obtained (for example, by dividing the corrected $I_{P2}$ gain by an $I_{P2}$ gain appearing in the standard $I_{P2}$ characteristic). By using the $I_{P2}$ gain correction coefficient, the second pumping current $I_{P2}$ corrected for offset is corrected for the $I_{P2}$ gain.

In step S190, by using the standard $I_{P2}$ characteristic (see FIG. 4), the NOx concentration is obtained from the second pumping current $I_{P2}$ which underwent various corrections as described above (i.e., from the corrected second pumping current $I_{P2}$). The thus-obtained NOx concentration is output as the concentration of NOx in the measurement gas.

According to the standard $I_{P2}$ characteristic, the NOx concentration and the second pumping current $I_{P2}$ are in a proportional relation. Therefore, the NOx concentration can be obtained without using the standard $I_{P2}$ characteristic. Specifically, after the $I_{P2}$ gain is obtained from the standard $I_{P2}$ gain characteristic, the thus obtained $I_{P2}$ gain is corrected based on the $I_{P2}$ gain correction data to obtain a corrected $I_{P2}$ gain. Based on the corrected $I_{P2}$ gain, the NOx concentration may be obtained from the second pumping current $I_{P2}$ corrected for offset.

In steps S200 to S270, the first and second pumping currents $I_{P2}$ and $I_{P2}$, respectively, detected in step S150 are compared with the maximum and minimum first pumping currents $I_{P1max}$ and $I_{P1min}$, respectively, and the maximum and minimum second pumping currents $I_{P2max}$ and $I_{P2min}$, respectively, which are temporarily stored in an unillustrated RAM of the ECU 50. If the $I_{P1}$ ($I_{P2}$) value is greater than the maximum value $I_{P1max}$ ($I_{P2max}$) or if the $I_{P1}$ ($I_{P2}$) value is smaller than the minimum value $I_{P1min}$ ($I_{P2min}$), the $I_{P1max}$ ($I_{P2max}$) or $I_{P1min}$ ($I_{P2min}$) value is updated accordingly.

Specifically, in step S200, the first pumping current $I_{P1}$ detected in step S150 is compared with the maximum first pumping current $I_{P1max}$. If the detected $I_{P1}$ value is greater than the $I_{P1max}$ value (decision of YES in step S200), processing will proceed to step S210, in which the detected $I_{P1}$ value is stored as a new $I_{P1max}$ value. If the detected $I_{P1}$ value is not greater than the $I_{P1max}$ value (decision of NO in step S200), processing will proceed to step S220 without updating the $I_{P1max}$ value.

In step S220, the first pumping current $I_{P1}$ detected in step S150 is compared with the minimum first pumping current $I_{P1min}$. If the detected $I_{P1}$ value is smaller than the $I_{P1min}$ value (decision of YES in step S220), processing will proceed to step S230, in which the detected $I_{P1}$ value is stored as a new $I_{P1min}$ value. If the detected $I_{P1}$ value is not smaller than the $I_{P1min}$ value (decision of NO in step S220), processing will proceed to step S240 without updating the $I_{P1min}$ value.

In step S240, the second pumping current $I_{P2}$ detected in step S150 is compared with the maximum second pumping current $I_{P2max}$. If the detected $I_{P2}$ value is greater than the $I_{P2max}$ value (decision of YES in step S240), processing will proceed to step S250, in which the detected $I_{P2}$ value is stored as a new $I_{P2max}$ value. If the detected $I_{P2}$ value is not greater than the $I_{P2max}$ value (decision of NO in step S240), processing will proceed to step S260 without updating the $I_{P2max}$ value.

In step S260, the second pumping current $I_{P2}$ detected in step S150 is compared with the minimum second pumping current $I_{P2min}$. If the detected $I_{P2}$ value is smaller than the $I_{P2min}$ value (decision of YES in step S260), processing will proceed to step S270, in which the detected $I_{p2}$ value is stored as a new $I_{P2min}$ value. If the detected $I_{P2}$ value is not smaller than the $I_{P2min}$ value (decision of NO in step S260), processing will proceed to step S280 without updating the $I_{P2min}$ value.

In step S280, time t measured by a timer is compared with a predetermined periodic time T. If the measured time t is less than the predetermined periodic time T (decision of YES in step S280), step S140 and subsequent steps will be performed again. If the measured time t is not less than the predetermined periodic time T (decision of NO in step S280), processing will proceed to step S300. In step S300, the maximum and minimum first pumping currents $I_{P1max}$ and $I_{P1min}$, respectively, and the maximum and minimum second pumping currents $I_{P2max}$ and $I_{P2min}$, respectively, stored in an unillustrated RAM of the ECU 50 are associated with the current record number n, and these values associated with the current record number n are written onto the floppy disk 52. Thus, the ECU 50 serves as writing means of the present invention.

Subsequently, processing proceeds to step S310, in which the record number n is incremented. Then, step S130 and subsequent steps are performed again.

As a result, at intervals of the predetermined periodic time T, the record number n is assigned to the maximum and minimum first pumping currents $I_{P1max}$ and $I_{P1min}$, respectively, and the maximum and minimum second pumping currents $I_{P2max}$ and $I_{P2min}$, respectively. Thus, the values of $I_{P1max}$, $I_{P1min}$, $I_{P2max}$, and $I_{P2min}$ are recorded on the floppy disk 52 in association with the record number n. Since a value obtained by multiplying the predetermined periodic time T by the record number n corresponds to elapsed time, the above-mentioned recording process is synonymous with the recording of changes in the values of $I_{P1max}$, $I_{P1min}$, $I_{P2max}$ and $I_{P2min}$ with the lapse of time.

In step S120, the maximum first pumping current $I_{P1max}$ and the maximum second pumping current $I_{P2max}$ are initialized to values smaller than those normally assumed by the first pumping current $I_{P1}$ and the second pumping current $I_{p2}$; the minimum first pumping current $I_{P1min}$ and the minimum second pumping current $I_{P2min}$ are initialized to values larger than those normally assumed by the first pumping current $I_{P1}$ and the second pumping current $I_{P2}$. Accordingly, when the record number n is 1, a judgment of YES is made in each of steps S200, S220, S240 and S260.

Thus, the detected $I_{P1}$ and $I_{P2}$ values replace the initial values of $I_{P1max}$, $I_{P1min}$, $I_{P2max}$ and $I_{p2min}$ and become new maximum and minimum values without fail. Thus, in step S300, these initial values are never written onto the floppy disk 52.

Correction data used in steps S160 to S180 are unique to the individual NOx sensors 2 and are recorded on floppy disks 52 corresponding to the individual NOx sensors 2. When the NOx sensor 2 is replaced with another NOx sensor 2 by disconnecting the connector 21a, the floppy disk 52 which accompanies the new NOx sensor 2 replaces the former floppy disk 52 so as to enable the new NOx sensor 2.

As described above, according to the present embodiment, the change in the first pumping current $I_{P1}$ is written onto the floppy disk 52 in the form of the maximum and minimum values $I_{P1max}$ and $I_{P1min}$ during each predetermined periodic time T. Also, the change in the second pumping current $I_{P2}$ is written onto the floppy disk 52 in the form of the maximum and minimum values $I_{P2max}$ and $I_{P2min}$ during each predetermined periodic time T. Thus, even when the NOx sensor 2 becomes unusable due to a failure or the like, a record of operating conditions of the unusable NOx sensor 2 is readily available from the accompanying floppy disk 52. This feature facilitates investigation of the cause of the failure. Therefore, a user can readily carry out necessary measures to improve the NOx sensor 2 accordingly. Also, performance (for example, durability and heat resistance) of the NOx sensor 2 can be accurately evaluated.

Because the elapsed time of use of the NOx sensor 2 can be obtained from the record number n and the predetermined periodic time T, a user can readily identify, for example, when the NOx sensor 2 became unusable or when a sign of instability first appeared.

Furthermore, because the maximum and minimum first pumping currents $I_{P1max}$ and $I_{P1min}$, respectively, and the maximum and minimum second pumping currents $I_{P2max}$ and $I_{P2min}$ are recorded at intervals of the predetermined periodic time T, the area occupied by the stored data on the floppy disk 52 can be reduced as compared to the case of recording every change in the first and second pumping currents $I_{P1}$ and $I_{P2}$.

By executing steps S160 to S190, even when the same measurement gas is measured for NOx concentration using different NOx sensors 2, variations in measurement among the NOx sensors 2 are corrected by means of correction data peculiar to the individual NOx sensors 2. Therefore, the NOx sensors 2 provide similar measurement results with a good degree of accuracy. Furthermore, instead of storing various characteristics ($I_{P1}$ characteristic, offset characteristic, temperature characteristic, and $I_{P2}$ gain characteristic) for individual NOx sensors 2, storage may be limited to merely the standard characteristics and correction data. Consequently, the storage capacity can be relatively small. Additionally, because correction data accompanying the corresponding NOx sensor 2 is stored on the floppy disk 52 (a flexible disk), the correction data can conveniently be carried.

In the present embodiment described above, changes in the first and second pumping currents $I_{P1}$ and $I_{P2}$, respectively, are recorded. Furthermore, changes in other parameters may be recorded in a manner similar to that described above which must be considered in determining the concentration of nitrogen oxides in the measurement gas. Examples of such parameters include the temperature of the Vs cell 6, or the element temperature, the concentration of oxygen in the measurement gas, and the concentration of nitrogen oxides in the measurement gas. As the number of parameters to be recorded increases, investigation of the cause of an NOx sensor 2 failure is further facilitated, and performance of the NOx sensor 2 can be evaluated more accurately.

In the present embodiment described above, the floppy disk 52 is used as recording means. However, optical disks or magneto-optical disks may be used. Also, fixed memory media such as hard disks may be used. A hard disk is not convenient for a user to carry, but may be sufficiently useful if the apparatus is designed to read out from the hard disk correction data corresponding to each NOx sensor 2.

Figure 5B:
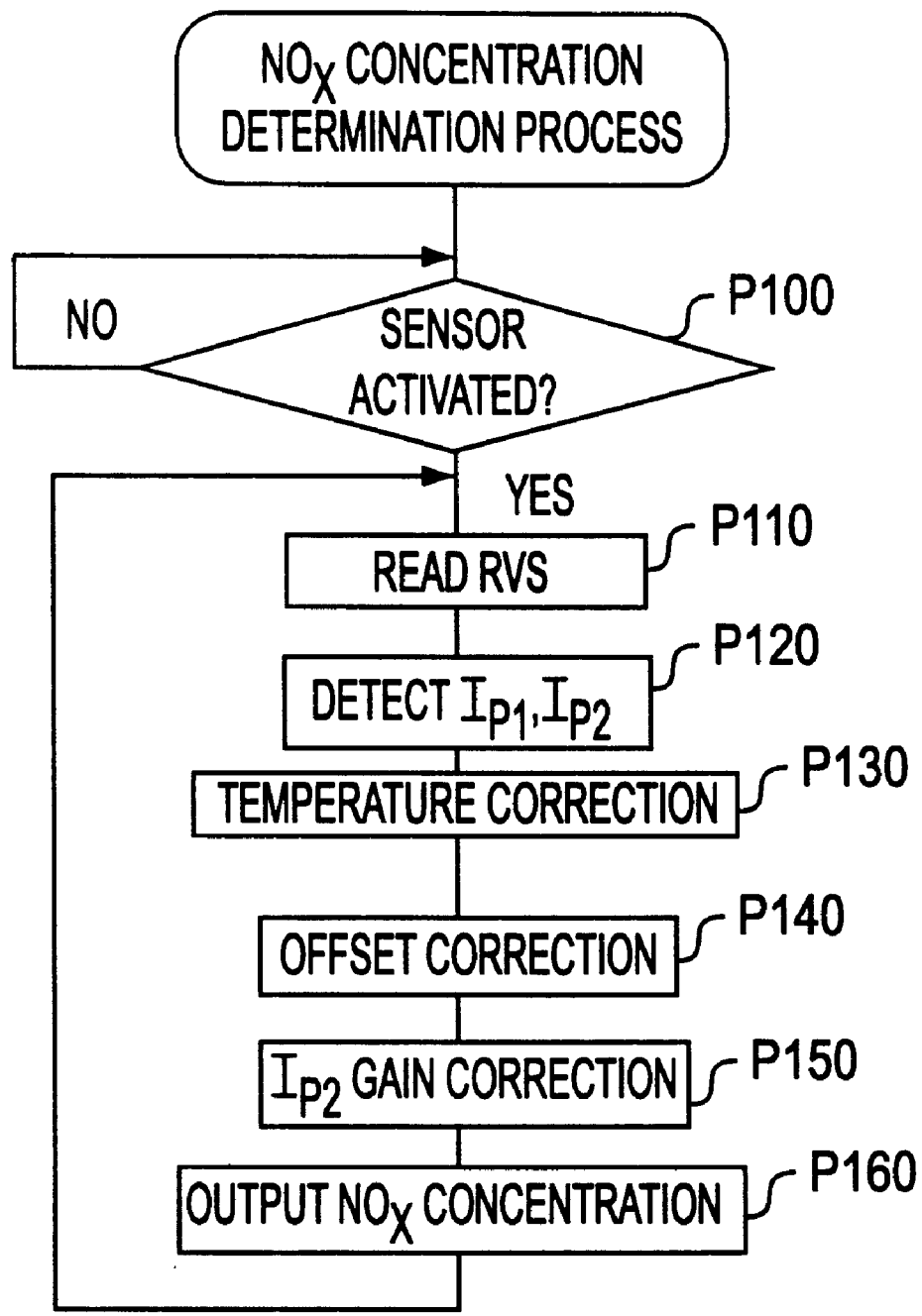
FIG. 5B is a flowchart showing a second main process which is repeatedly executed by an ECU.

Next, another main process executed by the ECU 50 of the NOx-concentration detecting apparatus will be described with reference to FIGS. 4 and 5B. FIG. 5B shows a flowchart of a second main process for determining NOx concentration.

Subsequent to starting the NOx-concentration detecting apparatus, in step P100 of the main process, an activation judgment process for the NOx sensor 2 is executed. Specifically, a judgment is made whether or not to active the NOx sensor 2 by applying current to the heaters 12 and 14. If the NOx sensor 2 is not activated, the processing is looped until the NOx sensor 2 is activated.

In the activation judgment process, for example, a determination is made as to whether or not the internal resistance $R_{VS}$ of the Vs cell 6 has dropped to or below a predetermined activation judgment value. The internal resistance $R_{VS}$ of the Vs cell 6 is reduced as the activation of the Vs cell 6 progresses with increasing element temperature. Thus, in step P100, after starting the supply of current to the heaters 12 and 14, a determination is made as to whether or not the internal resistance $R_{VS}$ of the Vs cell 6 has dropped to or below the activation judgment value, thereby judging whether or not the element temperature has reached a predetermined activation temperature.

Immediately after the NOx-concentration detecting apparatus is started, an unillustrated initialization process turns switch SW1 in the drive circuit 40 ON and turns switches SW2 and SW3 in the drive circuit 40 OFF. However, operation of the differential amplifier AMP in the drive circuit 40 is suspended until it is determined in the activation judgment process in step P100 that the temperature of the NOx sensor 2 has risen to near the activation temperature.

Next, when the NOx sensor 2 is judged active in step P100, processing proceeds to step P110, where the internal resistance $R_{VS}$ of the Vs cell 6 is read. In subsequent step P120, the detection signal $V_{Ip2}$ issued from the resistor R3 of the sensing circuit 42 is read to thereby detect the second pumping current $I_{p2}$. Also, the detection signal $V_{IP1}$ issued from the resistor R0 of the drive circuit 40 is read to thereby detect the first pumping current $I_{P1}$.

In step P130, based on the internal resistance $R_{VS}$ which was read in step P110, a temperature correction amount is calculated for the second pumping current $I_{p2}$. Then, based on the thus-obtained temperature correction amount, the second pumping current $I_{p2}$ is corrected for temperature.

Specifically, in order to accurately determine NOx concentration from the second pumping current Ip, even upon an abrupt change in the temperature of the measurement gas, the temperature of the Vs cell 6, i.e., the element temperature, is obtained from the internal resistance $R_{VS}$ of the Vs cell 6. A correction amount for the element temperature is obtained based on the standard temperature characteristic stored in an unillustrated ROM. The thus-obtained temperature correction amount is corrected based on the temperature characteristic correction data read from the floppy disk 52 to obtain a corrected temperature correction amount. By using the corrected temperature correction amount, a correction for the temperature is carried out. When the NOx sensor 2 is a standard NOx sensor, the corrected temperature correction amount becomes equal to the temperature correction amount obtained on the basis of the standard temperature characteristic.

After the above correction for temperature, processing proceeds to step P140, in which the second pumping current $I_{p2}$ is corrected for offset. Specifically, the $I_{P1}$ characteristic correction data is read from the floppy disk 52, and the first pumping current $I_{P1}$ is corrected based on the read $I_{P1}$ characteristic correction data to obtain the corrected first pumping current $I_{P1}$. The concentration of oxygen in the measurement gas is obtained from the corrected first pumping current $I_{P1}$ by using the standard $I_{P1}$ characteristic. The offset current $I_{P2OFF}$ is obtained from the thus-obtained oxygen concentration by using the standard offset characteristic. The thus-obtained offset current $I_{P2OFF}$ is corrected based on the offset characteristic correction data read from the floppy disk 52 to obtain the corrected offset current $I_{P2OFF}$. By using the corrected offset current $I_{P2OFF}$, the second pumping current $I_{p2}$ corrected for temperature is corrected for offset. When the NOx sensor is a standard NOx sensor, the corrected offset current value becomes equal to the offset current value obtained on the basis of the standard offset characteristics.

In subsequent P150, the second pumping current $I_{p2}$ corrected for offset is corrected for $I_{p2}$ gain. Specifically, by using the standard $I_{p2}$ gain characteristic, the $I_{p2}$ gain is obtained from the oxygen concentration which, in turn, was obtained from the first pumping current $I_{P1}$ in step P140. The thus-obtained $I_{p2}$ gain is corrected based on the $I_{p2}$ gain correction data read from the floppy disk 52 to obtain a corrected $I_{p2}$ gain. By using the corrected $I_{p2}$ gain, an $I_{p2}$ gain correction coefficient is obtained (for example, by dividing the corrected $I_{p2}$ gain by an $I_{p2}$ gain appearing in the standard $I_{p2}$ characteristic). By using the $I_{p2}$ gain correction coefficient, the second pumping current $I_{p2}$ corrected for offset is subjected to $I_{p2}$ gain correction. When the NOx sensor 2 is a standard NOx sensor, the corrected $I_{p2}$ gain is equal to the $I_{p2}$ gain obtained on the basis of the standard $I_{p2}$ gain characteristic.

In step P160, by using the standard $I_{P2}$ characteristic, the NOx concentration is obtained from the second pumping current $I_{P2}$ which underwent the $I_{P2}$ gain correction (i.e., from the corrected second pumping current $^1P2$). The thus-obtained NOx concentration is output as the concentration of NOx in the measurement gas.

According to the standard $I_{P2}$ characteristic, the NOx concentration and the second pumping current $I_{P2}$ are in a proportional relation. Therefore, the NOx concentration can be obtained without using the standard $I_{P2}$ characteristic. Specifically, after the $I_{P2}$ gain is obtained from the standard $I_{P2}$ gain characteristic, the thus obtained $I_{P2}$ gain is corrected based on the $I_{P2}$ gain correction data to obtain a corrected $I_{P2}$ gain. Based on the corrected $I_{P2}$ gain, the NOx concentration may be obtained from the second pumping current $I_{P2}$ corrected for offset.

Because the above-mentioned correction data are peculiar to individual NOx sensors, a single floppy disk 52 which contains unique correction data accompanies each of the NOx sensors. When the NOx sensor 2 is replaced with another by disconnecting the connector 21a, the floppy disk 52 accompanying the former NOx sensor 2 is replaced with that accompanying the new NOx sensor 2 before the NOx-concentration detecting apparatus is started.

As described above, according to the present embodiment, even when the same measurement gas is measured for NOx concentration using different NOx sensors 2, variations in measurement among the NOx sensors 2 are corrected by means of correction data peculiar to the individual NOx sensors 2. Therefore, the NOx sensors 2 provide similar measurement results with a good degree of accuracy. Furthermore, instead of storing various characteristics ($I_{P_1}$ characteristic, offset characteristic, temperature characteristic, and $I_{p2}$ gain characteristic) for individual NOx sensors 2, storage may be limited to merely the standard characteristics and correction data. Consequently, the storage capacity can be relatively small. Furthermore, because correction data accompanying the corresponding NOx sensor 2 is stored on the floppy disk 52 (a flexible disk), the correction data can conveniently be carried, and applicability of the correction data is highly improved.

In the present embodiment described above, the floppy disk 52 is used as the correction data storage means. However, optical disks or magneto-optical disks may be used. Optical or magneto-optical disks are very handy and enable correction data to be readily associated with the individual NOx sensors 2. Also, fixed memory media such as hard disks may be used as the correction data storage means. A hard disk is not convenient for a user to carry, but may be sufficiently useful if the apparatus is designed to read out from the hard disk correction data corresponding to each NOx sensors 2.

The NOx-concentration detecting apparatus of the present embodiment is well adapted, for example, for use in indoor and outdoor gas measurement equipment.

Figure 6:
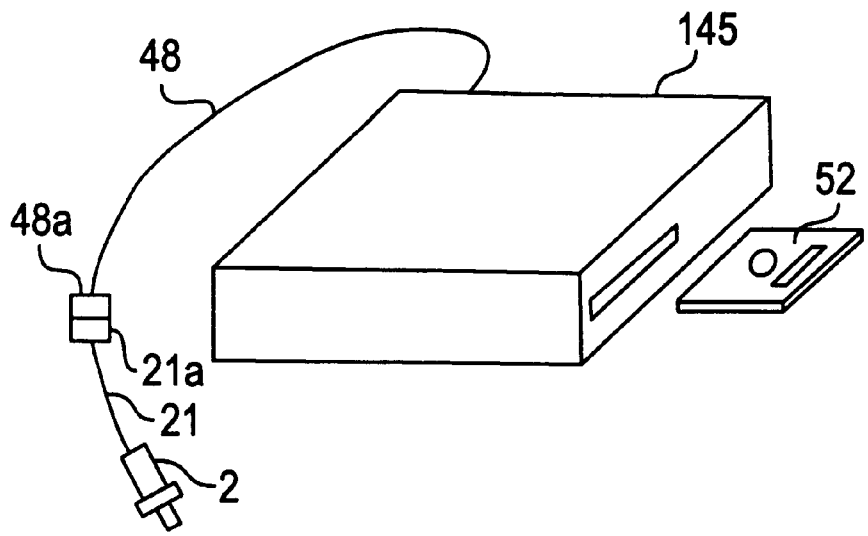
FIG. 6 is a schematic view showing the entire external configuration of an NOx-concentration detecting apparatus according to a second embodiment of the present invention.

Second Embodiment:

A second embodiment of the present invention has an internal configuration similar to that of the first embodiment, but has an external configuration different from that of the first embodiment. FIG. 6 schematically shows the external configuration of this embodiment. Specifically, a control box 145 includes the drive circuit 40, the sensing circuit 42, the heater-energizing circuit 44, the electronic control unit 50 and the floppy disk drive 52 shown in FIG. 1. As in the case of the first embodiment, the control box 145 and the NOx sensor 2 are electrically connected by means of the cables 21 and 48 which, in turn, are connected by means of the connectors 21a and 48a. The thus-configured second embodiment yields actions and effects similar to those of the first embodiment.

Figure 7:
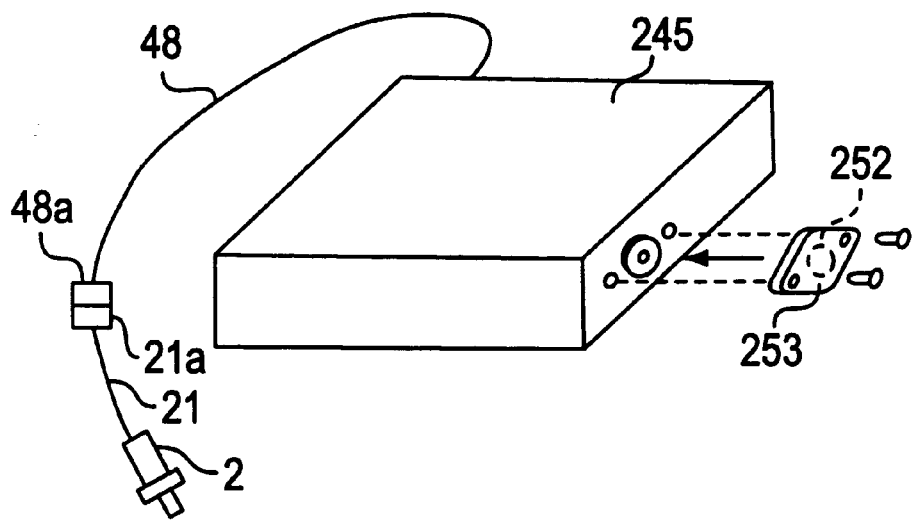
FIG. 7 is a schematic view showing the entire external configuration of an NOx-concentration detecting apparatus according to a third embodiment of the present invention.

Third Embodiment:

A third embodiment of the present invention is configured in a manner similar to that of the second embodiment, but is different in that a substantially button-shaped semiconductor recording medium is used instead of a floppy disk. FIG. 7 schematically shows the external configuration of this embodiment. Specifically, a control box 245 includes the drive circuit 40, the sensing circuit 42, the heater-energizing circuit 44 and the electronic control unit 50 shown in FIG. 1. In the present embodiment, various correction data (see the description of the first embodiment) peculiar to the NOx sensor 2 are stored in a substantially button-shaped semiconductor recording medium 252 (for example, TOUCH MEMORY BUTTON, DS1995, (trade name, product of Dallas Semiconductor Corporation)). The semiconductor recording medium 252 has a diameter as small as about 2 cm and is embedded in a substantially rhombic mount 253 (TOUCH MEMORY MOUNT PRODUCT, DS9093x, (trade name, product of Dallas Semiconductor Corporation)). The mount 253 is screwed onto the outer surface of the control box 245. Accordingly, the semiconductor recording medium 252 is removably mounted on the control box 245. As in the case of the first embodiment, the control box 245 and the NOx sensor 2 are electrically connected by means of the cables 21 and 48 which, in turn, are connected by means of the connectors 21a and 48a.

As described in the section of the first embodiment, correction data are different among the individual NOx sensors 2. Accordingly, a recording medium in which such unique correction data are stored preferably accompanies the relevant NOx sensor 2. In this regard, the present embodiment uses the substantially button-shaped semiconductor recording medium 252 which is smaller than the floppy disk 52 and thus further conveniently accompanies the NOx sensor 2.

The thus-configured third embodiment yields actions and effects similar to those of the first embodiment. Furthermore, because the semiconductor recording medium 252 is smaller than a floppy disk, the semiconductor recording medium 252 does not become a nuisance even when it accompanies each NOx sensor 2.

Figure 8A:
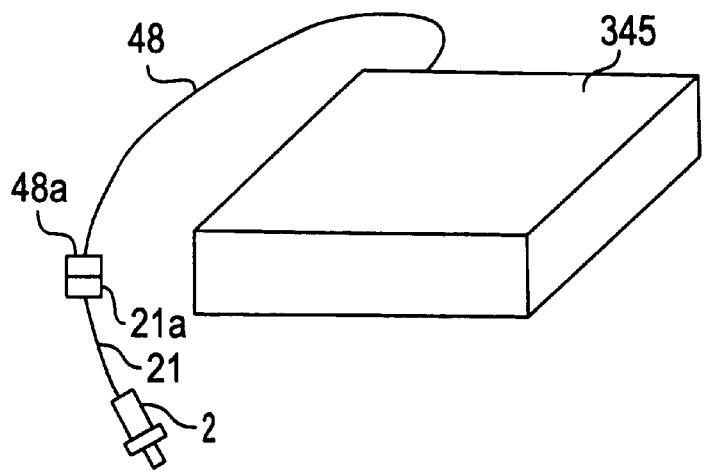
FIG. 8A is a schematic view showing the entire external configuration of an NOx-concentration detecting apparatus according to a fourth embodiment of the present invention.
Figure 8B:
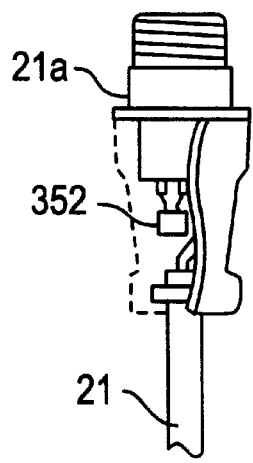
FIG. 8B is a partially cutaway view showing a male-type connector having a built-in recording medium.
Figure 8C:
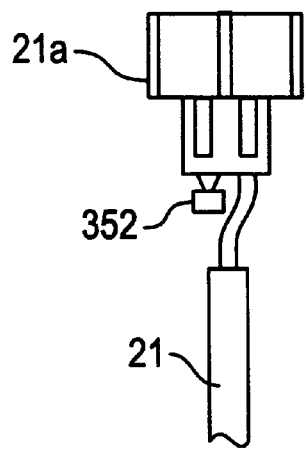
FIG. 8C is a partially cutaway view showing a female-type connector having a built-in recording medium.

Fourth Embodiment:

A fourth embodiment of the present invention is configured in a manner similar to that of the second embodiment, but is different in that a semiconductor recording medium built into a connector is used instead of a floppy disk. FIGS. 8A–8C schematically show the external configuration of the present embodiment. Specifically, a control box 345 of FIG. 8A includes the drive circuit 40, the sensing circuit 42, the heater-energizing circuit 44 and the electronic control unit 50 shown in FIG. 1. In the present embodiment, various correction data (see the description of the first embodiment) peculiar to the NOx sensor 2 are stored in a semiconductor recording medium 352 (for example, TOUCH MEMORY PROBE DS9092, or ADD ONLY MEMORY DS2505, (trade names, products of Dallas Semiconductor Corporation) ) built into the connector 21a of the NOx sensor 2. FIG. 8B shows the semiconductor recording medium 352 built into the male-type connector 21a of the NOx sensor 2, and FIG. 8C shows the semiconductor recording medium 352 built into the female-type connector 21a of the NOx sensor 2. In either case, the semiconductor recording medium 352 is connected to unused pins of a plurality of pins (not shown) provided in the connector 21a to thereby establish an electrical connection with the control box 345 via the connector 21a. Since the semiconductor recording medium 352, in which correction data are recorded, is built into the connector 21a united to the NOx sensor 2, the NOx sensor is accompanied by correction data without fail. Thus, in addition to the advantage of small size, the present embodiment has the advantage that when the NOx sensor 2 is replaced, correction data are inevitably replaced. The NOx-concentration detecting apparatus of the present embodiment is suitable for use on board an automobile.

While the invention has been described in detail and with reference to specific embodiments thereof, it will be apparent to one skilled in the art that various changes and modifications can be made therein without departing from the spirit and scope thereof.

What is claimed is:

1. An NOx-concentration detecting apparatus comprising:
   an NOx sensor comprising:
      a first measurement space in communication with the measurement gas via a first diffusion-controlling layer,
      a first oxygen-pumping cell for pumping oxygen out of said first measurement space,
      an oxygen-concentration measuring cell for measuring the oxygen concentration in said first measurement space, a second measurement space in communication with said first measurement space via a second diffusion-controlling layer, and a second oxygen-pumping cell for pumping oxygen out of said second measurement space;

pumping-current control means for controlling the concentration of oxygen contained in said first measurement space to a constant value, constant-voltage application means for applying a constant voltage to said second oxygen-pumping cell, an NOx-concentration detecting means for determining the concentration of NOx in the measurement gas based at least in part on the value of current flowing through said second oxygen-pumping cell as a result of applying a constant voltage to said second oxygen-pumping cell, and writing means for writing to a recorder variation of at least one parameter selected from the parameter group consisting of a first pumping current value which is the current flowing through said first oxygen-pumping cell when the concentration of oxygen in said first measurement space is controlled at a constant level by said pumping-current control means, a second pumping current value which is the current flowing through said second oxygen-pumping cell when a constant voltage is applied to said second oxygen-pumping cell by said constant-voltage application means, the concentration of oxygen contained in the measurement gas which is determined based on said first pumping current value, and the concentration of NOx in the measurement gas which is determined based on said second pumping current value, said NOx-concentration detecting apparatus further comprising standard-characteristic storage means for storing predetermined standard characteristics representing correlations among said first pumping current value, said second pumping current value, and the concentration of NOx in the measurement gas, wherein said recorder contains correction data for making previously measured characteristics of said NOx sensor equal to said standard characteristics, which characteristics represent correlations among said first pumping current value, said second pumping current value, and the concentration of NOx in the measurement gas; and said NOx-concentration detecting means comprises means for detecting said first pumping current value and said second pumping current value, means for correcting the detected values based on said correction data stored in said correction data recording means, and means for determining the concentration of NOx in the measurement gas using the standard characteristics stored in said standard-characteristic storage means.

2. The NOx-concentration detecting apparatus according to claim 1, wherein each of said first and second oxygen-pumping cells and said oxygen-concentration-measuring cell comprises an oxygen-ion conductive solid electrolyte layer and porous electrodes disposed on opposite surfaces of the oxygen-ion conductive solid electrolyte layer.

3. The NOx-concentration detecting apparatus according to claim 1, wherein said pumping-current control means comprises means for maintaining an output voltage from said oxygen-concentration-measuring cell at a constant value.

4. The NOx-concentration detecting apparatus according to claim 1, further comprising a heater for heating said NOx sensor to a temperature at which the detection of the concentration of NOx in the measurement gas is enabled.

5. The NOx-concentration detecting apparatus according to claim 1, which comprises means for writing to said recorder at predetermined intervals variation of at least one parameter selected from said parameter group.

6. The NOx-concentration detecting apparatus according to claim 1, which comprises means for writing to said recorder at predetermined intervals variation of at least one parameter selected from said parameter group in the form of a maximum value and a minimum value in each interval.

7. The NOx-concentration detecting apparatus according to claim 1, wherein said NOx sensor is removably connected to said NOx-concentration detecting means via a connector.

8. The NOx-concentration detecting apparatus according to claim 5, wherein said NOx sensor is removably connected to said NOx-concentration detecting means via a connector.

9. The NOx-concentration detecting apparatus according to claim 6, wherein said NOx sensor is removably connected to said NOx-concentration detecting means via a connector.

10. The NOx-concentration detecting apparatus according to claim 7, wherein said recorder comprises a removably mounted recording medium.

11. The NOx-concentration detecting apparatus according to claim 7, wherein said recorder comprises a button-like recording medium adapted to be removably mounted via a mount.

12. The NOx-concentration detecting apparatus according to claim 1, wherein said NOx sensor is removably connected to said NOx-concentration detecting means via a connector, and said recorder is built into said connector.

13. An NOx-concentration detecting apparatus comprising:

an NOx sensor for measuring one or more parameters of a measurement gas;

standard-characteristic storage means for storing predetermined standard characteristics which represent correlations among the one or more parameters measured by a standard sensor and the concentration of NOx in the measurement gas;

correction data storage means for storing correction data for making previously measured characteristics of said NOx sensor equal to said standard characteristics; and NOx-concentration detecting means for determining the NOx concentration of said measurement gas based on at least one of the parameters measured by said NOx sensor and data stored in said standard-characteristic storage means.

14. The NOx-concentration detecting apparatus according to claim 13, wherein said NOx sensor and said correction data storage means are removably mounted.

15. The NOx-concentration detecting apparatus according to claim 13, wherein said correction data storage means comprises a substantially button-like recording medium adapted to be removably mounted via a mount.

16. The NOx-concentration detecting apparatus according to claim 13, wherein said NOx sensor is removably connected to said NOx-concentration detecting means via a connector, and said correction data storage means is built into said connector.

17. An NOx-concentration detecting apparatus comprising:

an NOx sensor comprising:

a first measurement space in communication with the measurement gas via a first diffusion-controlling layer, a first oxygen-pumping cell for pumping oxygen out of said first measurement space, an oxygen-concentration measuring cell for measuring the oxygen concentration in said first measurement space, a second measurement space in communication with said first measurement space via a second diffusion-controlling layer, and a second oxygen-pumping cell for pumping oxygen out of said second measurement space; and pumping-current control means for controlling the concentration of oxygen contained in said first measurement space to a constant value, constant-voltage application means for applying a constant voltage to said second oxygen-pumping cell, standard-characteristic storage means for storing predetermined standard characteristics which represent correlations among a first pumping current which is the current flowing through said first oxygen-pumping cell when the concentration of oxygen in said first measurement space is controlled at a constant level by said pumping-current control means, a second pumping current which is the current flowing through said second oxygen-pumping cell when a constant voltage is applied to said second oxygen-pumping cell by said constant-voltage application means, and the concentration of NOx in the measurement gas, correction data storage means for storing correction data for making previously measured characteristics of the NOx sensor equal to said standard characteristics, which characteristics represent correlations among said first pumping current, said second pumping current and said concentration of NOx in the measurement gas, and NOx-concentration detecting means for detecting said first pumping current and said second pumping current, for correcting the detected current values based on the correction data stored in said correction data storage means, and for determining the concentration of NOx in the measurement gas using the standard characteristics stored in said standard-characteristic storage means.

18. The NOx-concentration detecting apparatus according to claim 17, wherein each of said first and second oxygen-pumping cells and said oxygen-concentration-measuring cell comprises an oxygen-ion conductive solid electrolyte layer and porous electrodes disposed on opposite surfaces of the oxygen-ion conductive solid electrolyte layer.

19. The NOx-concentration detecting apparatus according to claim 17, wherein said pumping-current control means comprises means for maintaining an output voltage from said oxygen-concentration-measuring cell at a constant value.

20. The NOx-concentration detecting apparatus according to claim 17, further comprising a heater for heating said NOx sensor to a temperature at which the detection of the concentration of NOx in the measurement gas is enabled.

21. The NOx-concentration detecting apparatus according to claim 17, wherein said characteristics representing correlations among said first pumping current, said second pumping current and the concentration of NOx in the measurement gas include at least a correlation between the concentration of oxygen in the measurement gas and said first pumping current, a correlation between the concentration of NOx in the measurement gas and said second pumping current, and a correlation between the concentration of oxygen in the measurement gas and said second pumping current.

22. The NOx-concentration detecting apparatus according to claim 18, wherein said correlation between the concentration of NOx in the measurement gas and said second pumping current includes a correlation between the concentration of oxygen in the measurement gas and the rate of change in said second pumping current relative to the concentration of NOx in the measurement gas.

23. The NOx-concentration detecting apparatus according to claim 18, wherein said characteristics representing the correlation among said first pumping current, said second pumping current and the concentration of NOx in the measurement gas further include a correlation between the temperature of said NOx sensor and said second pumping current.

24. The NOx-concentration detecting apparatus according to claim 19, wherein said characteristics representing the correlation among said first pumping current, said second pumping current and the concentration of NOx in the measurement gas further include a correlation between the temperature of said NOx sensor and said second pumping current.

25. The NOx-concentration detecting apparatus according to any one of claims 17 and 21 to 24, wherein said NOx sensor and said correction data storage means are removably mounted.

26. The NOx-concentration detecting apparatus according to claim 17, wherein said correction data storage means comprises a substantially button-like recording medium adapted to be removably mounted via a mount.

27. The NOx-concentration detecting apparatus according to claim 17, wherein said NOx sensor is removably connected to said NOx-concentration detecting means via a connector, and said correction data storage means is built into said connector.

28. An NOx-concentration detecting apparatus comprising:

an NOx sensor for measuring one or more parameters of a measurement gas;

characteristic storage means for storing previously measured characteristics of said NOx sensor which represent correlations among the one or more parameters measured by said NOx sensor and the concentration of NOx in the measurement gas; and NOx-concentration detecting means for determining the NOx concentration of said measurement gas based on at least one of the parameters measured by said NOx sensor and data stored in said characteristic storage means, wherein said characteristic storage means comprises standard-characteristic storage means for storing predetermined standard characteristics which represent correlations among one or more parameters measured by a standard sensor and the concentration of NOx in the measurement gas; and correction data storage means for storing correction data for making previously measured characteristics of said NOx sensor equal to said standard characteristics.

29. The NOx-concentration detecting apparatus according to claim 28, wherein said NOx sensor is removably connected to said NOx-concentration detecting means via a connector, and said correction data storage means is built into said connector.

* * * * *